(12) United States Patent
Schneider et al.

(10) Patent No.: US 12,064,514 B2
(45) Date of Patent: Aug. 20, 2024

(54) ULTRASOUND-SENSITIVE PEPTIDE PARTICLES FOR SPATIALLY RESOLVED MOLECULE DELIVERY

(71) Applicants: The Penn State Research Foundation, University Park, PA (US); THE UNITED STATES OF AMERICA, AS REPRESENTED BY THE SECRETARY, DEPARTMENT OF HEALTH AND HUMAN SERVICES, Bethesda, MD (US)

(72) Inventors: Joel P. Schneider, Frederick, MD (US); Scott H. Medina, State College, PA (US)

(73) Assignees: THE PENN STATE RESEARCH FOUNDATION, University Park, PA (US); THE UNITED STATES OF AMERICA, AS REPRESENTED BY THE SECRETARY, DEPARTMENT OF HEALTH AND HUMAN SERVICES, OFFICE OF TECHNOLOGY TRANSFER, NATIONAL INSTITUTES OF HEALTH, Bethesda, MD (US)

( * ) Notice: Subject to any disclaimer, the term of this patent is extended or adjusted under 35 U.S.C. 154(b) by 0 days.

(21) Appl. No.: 16/634,679

(22) PCT Filed: Jul. 30, 2018

(86) PCT No.: PCT/US2018/044382
§ 371 (c)(1),
(2) Date: Jan. 28, 2020

(87) PCT Pub. No.: WO2019/023706
PCT Pub. Date: Jan. 31, 2019

(65) Prior Publication Data
US 2020/0197307 A1    Jun. 25, 2020

Related U.S. Application Data

(60) Provisional application No. 62/538,116, filed on Jul. 28, 2017.

(51) Int. Cl.
| C07K 7/08 | (2006.01) |
| A61K 9/00 | (2006.01) |
| A61K 9/127 | (2006.01) |
| A61K 47/65 | (2017.01) |
| C07K 7/06 | (2006.01) |
| B82Y 5/00 | (2011.01) |

(52) U.S. Cl.
CPC .......... *A61K 9/1273* (2013.01); *A61K 9/0009* (2013.01); *A61K 47/65* (2017.08); *C07K 7/06* (2013.01); *B82Y 5/00* (2013.01); *C07K 2319/01* (2013.01)

(58) Field of Classification Search
None
See application file for complete search history.

(56) References Cited

U.S. PATENT DOCUMENTS

| 5,997,898 | A |  | 12/1999 | Unger |  |
|---|---|---|---|---|---|
| 2003/0181423 | A1 | * | 9/2003 | Clapper | .................... C08J 7/12 |
|  |  |  |  |  | 435/180 |
| 2008/0194500 | A1 |  | 8/2008 | Mecozzi et al. |  |
| 2008/0299177 | A1 | * | 12/2008 | Hardy | .................. A61K 9/0009 |
|  |  |  |  |  | 424/427 |
| 2012/0264724 | A1 | * | 10/2012 | Nebolsin | ................ C07F 15/025 |
|  |  |  |  |  | 514/185 |
| 2015/0037419 | A1 | * | 2/2015 | Bazile | .................. C07D 249/04 |
|  |  |  |  |  | 424/489 |
| 2018/0111963 | A1 | * | 4/2018 | Stupp | ..................... A01N 25/10 |

FOREIGN PATENT DOCUMENTS

WO    WO 2013/181461    * 12/2013

OTHER PUBLICATIONS

Medina et al. ('Fluorous phase-directed peptide assembly affords nano-peptisomes capable of ultrasound-triggered cellular delivery' Angew Chem Int Ed Engl Sep. 11, 2017 v56(38) printed as pp. 1-13) (Year: 2017).*
Reches et al. ('Designed aromatic homo-dipeptides: formation of ordered nanostructures and potential nanotechnological applications' Physical Biology v3 2006 pp. s10-s19) (Year: 2006).*
Chen et al. ('Fusion protein linkers:property, design and functionality' Adv Drug Deliv Rev v65(10) Oct. 15, 2013 printed as pp. 1-32) (Year: 2013).*
Rapoport N ('Phase-shift, stimuli-responsive perfluorocarbon nanodroplets for drug delivery to cancer' Wiley Interdiscip Rev Nanomed Nanobiotehcnol v4(5) 2012 printed as pp. 1-33) (Year: 2012).*

(Continued)

*Primary Examiner* — Ronald T Niebauer
(74) *Attorney, Agent, or Firm* — Troutman Pepper Hamilton Sanders LLP

(57) ABSTRACT

The present invention is directed to peptisomes, including nanopeptisomes, which have a perfluorocarbon liquid core containing a perfluorocarbon liquid and a cargo, such as a therapeutically active agent, dispersed in the perfluorocarbon. liquid, and a plurality of amphiphilic peptide molecules surrounding the perfluorocarbon liquid core, wherein the amphiphilic peptide is represented by Formula (I) HB-CL-HP wherein HB is a fluorinated hydrophobic block, such as a fluorinated hydrophobic amino acid sequence, CL is a cross-linking motif, and HP is a hydrophilic amino acid sequence. The present invention is also directed to methods of use of the amphiphilic peptides and peptisomes, such as nanopeptisomes, to deliver a cargo, such as a therapeutically active agent, to a cell, Q wherein the cell may be in vitro, ex vivo, or in vivo.

12 Claims, 21 Drawing Sheets
Specification includes a Sequence Listing.

(56) References Cited

OTHER PUBLICATIONS

El Idrissi et al. ('Nanosensors based on polymer vesicles and planar membranes: a short review' Journal of Nanobiotechnology v16 (63) 2018 pp. 1-14) (Year: 2018).*

Sloand et al. ('Ultrasound-guided cytosolic protein delivery via transient fluorous masks' ACS Nano v4 2020 pp. 4061-4073) (Year: 2020).*

Bachem peptide calculator (entry for SISSLTD retrieved from htttps://www.bachem.com/knowledge-center/peptide-calculator/ on Jun. 9, 2022, 1 page) (Year: 2022).*

Tincu et al. ('Antimicrobial peptides from marine invertebrates' Antimicrobial agents and chemotherapy v48(10) Oct. 2004 pp. 3645-3654) (Year: 2004).*

Henderson et al. ('Fibronectin: a multidomain host adhesion targeted by bacterial fibronectin-binding proteins' FEMS Microbiol Rev v35 2011 pp. 147-200) (Year: 2011).*

Specification for 62410902 retrieved from https://patentcenter.uspto.gov/applications/62410902/ifw/docs on Dec. 14, 2022, 41 pages (Year: 2022).*

Claims for 62410902 retrieved from https://patentcenter.uspto.gov/applications/62410902/ifw/docs on Dec. 14, 2022, 4 pages numbered 42-45 (Year: 2022).*

Drawings for 62410902 retrieved from https://patentcenter.uspto.gov/applications/62410902/ifw/docs on Dec. 14, 2022, 13 pages (Year: 2022).*

Ulijn, R. et al., Designing peptide based nanomaterials, Chem. Soc. Rev., 37: 664-675, 2008.

Luo, T. et al., Collagen-like peptides and peptide-polymer conjugates in the design of assembled materials, Eur Polym J.,49(10): 2998-3009, Oct. 2013.

International Search Report, PCT/US2018/044382, Dec. 27, 2018.

* cited by examiner

SEQUENCE LISTING

```
<160> NUMBER OF SEQ ID NOS: 50

<210> SEQ ID NO 1
<211> LENGTH: 4
<212> TYPE: PRT
<213> ORGANISM: Artificial Sequence
<220> FEATURE:
<223> OTHER INFORMATION: targeting motif

<400> SEQUENCE: 1

Arg Gly Arg Arg
1

<210> SEQ ID NO 2
<211> LENGTH: 5
<212> TYPE: PRT
<213> ORGANISM: Artificial Sequence
<220> FEATURE:
<223> OTHER INFORMATION: targeting motif

<400> SEQUENCE: 2

Arg Gly Arg Arg Ser
1               5

<210> SEQ ID NO 3
<211> LENGTH: 5
<212> TYPE: PRT
<213> ORGANISM: Artificial Sequence
<220> FEATURE:
<223> OTHER INFORMATION: targeting motif

<400> SEQUENCE: 3

Tyr Gln Leu Asp Val
1               5

<210> SEQ ID NO 4
<211> LENGTH: 4
<212> TYPE: PRT
<213> ORGANISM: Artificial Sequence
<220> FEATURE:
<223> OTHER INFORMATION: targeting motif
```

```
<400> SEQUENCE: 4

Val Gly Val Ala
1

<210> SEQ ID NO 5
<211> LENGTH: 8
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 5

Gly His Gly Lys His Lys Asn Lys
1               5

<210> SEQ ID NO 6
<211> LENGTH: 9
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 6

Cys Arg Gly Asp Lys Gly Pro Asp Cys
1               5

<210> SEQ ID NO 7
<211> LENGTH: 7
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 7

Cys Lys Gly Ala Lys Ala Arg
1               5

<210> SEQ ID NO 8
<211> LENGTH: 9
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 8

Cys Arg Val Ser Arg Gln Asn Lys Cys
1               5

<210> SEQ ID NO 9
<211> LENGTH: 9
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 9

Cys Gly Gly Glu Arg Gly Lys Ser Cys
1               5

<210> SEQ ID NO 10
<211> LENGTH: 6
```

```
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 10

Cys Arg Ser Arg Lys Gly
1               5

<210> SEQ ID NO 11
<211> LENGTH: 6
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 11

Cys Lys Ala Ala Lys Asn
1               5

<210> SEQ ID NO 12
<211> LENGTH: 7
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 12

Cys Arg Gly Arg Arg Ser Thr
1               5

<210> SEQ ID NO 13
<211> LENGTH: 8
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 13

Cys Glu Tyr Gln Leu Asp Val Glu
1               5

<210> SEQ ID NO 14
<211> LENGTH: 7
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 14

Thr Val Arg Thr Ser Ala Asp
1               5

<210> SEQ ID NO 15
<211> LENGTH: 7
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 15

Pro Ile Glu Asp Arg Pro Met
```

```
1               5

<210> SEQ ID NO 16
<211> LENGTH: 7
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 16

Ala Leu Arg Asp Arg Pro Met
1               5

<210> SEQ ID NO 17
<211> LENGTH: 7
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 17

Pro Glu Lys Phe Arg Pro Met
1               5

<210> SEQ ID NO 18
<211> LENGTH: 7
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 18

Ile Lys Val Gly Lys Leu Gln
1               5

<210> SEQ ID NO 19
<211> LENGTH: 12
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 19

Ser Val Ser Val Gly Met Lys Pro Ser Pro Arg Pro
1               5                   10

<210> SEQ ID NO 20
<211> LENGTH: 7
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 20

Val Pro Glu Gln Arg Pro Met
1               5

<210> SEQ ID NO 21
<211> LENGTH: 9
<212> TYPE: PRT
<213> ORGANISM: Artificial Sequence
<220> FEATURE:
<223> OTHER INFORMATION: hydrophilic amino acid sequence including a
```

-continued

```
targeting agent

<400> SEQUENCE: 21

Cys Ala Lys Ile Asp Pro Glu Leu Cys
1               5

<210> SEQ ID NO 22
<211> LENGTH: 9
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 22

Cys Ser Asn Ile Asp Ala Arg Ala Cys
1               5

<210> SEQ ID NO 23
<211> LENGTH: 6
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 23

Arg Leu Gln Leu Lys Leu
1               5

<210> SEQ ID NO 24
<211> LENGTH: 8
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 24

Pro Met Met Arg Gln Arg Pro Met
1               5

<210> SEQ ID NO 25
<211> LENGTH: 7
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 25

Ala Lys Ala Thr Cys Pro Ala
1               5

<210> SEQ ID NO 26
<211> LENGTH: 7
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 26

Gln Pro Pro Met Glu Tyr Ser
1               5

<210> SEQ ID NO 27
```

```
<211> LENGTH: 7
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 27

Ser Ile Ser Ser Leu Thr Asp
1               5

<210> SEQ ID NO 28
<211> LENGTH: 8
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 28

Phe Arg Val Gly Val Ala Asp Val
1               5

<210> SEQ ID NO 29
<211> LENGTH: 13
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 29

Cys Asn Gly Arg Cys Val Ser Gly Cys Ala Gly Arg Cys
1               5                   10

<210> SEQ ID NO 30
<211> LENGTH: 7
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 30

Asn Trp Gly Asp Arg Ile Leu
1               5

<210> SEQ ID NO 31
<211> LENGTH: 9
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 31

Cys Val Ser Asn Pro Arg Trp Lys Cys
1               5

<210> SEQ ID NO 32
<211> LENGTH: 9
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 32
```

```
Cys Asp Cys Arg Gly Asp Cys Phe Cys
1               5
```

<210> SEQ ID NO 33
<211> LENGTH: 12
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 33

```
Tyr Ser Ala Tyr Pro Asp Ser Val Pro Met Met Ser
1               5                   10
```

<210> SEQ ID NO 34
<211> LENGTH: 7
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 34

```
Pro Leu Ala Ser Arg Pro Met
1               5
```

<210> SEQ ID NO 35
<211> LENGTH: 5
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 35

```
Lys Gly Arg Gly Asp
1               5
```

<210> SEQ ID NO 36
<211> LENGTH: 4
<212> TYPE: PRT
<213> ORGANISM: Artificial Sequence
<220> FEATURE:
<223> OTHER INFORMATION: hydrophilic amino acid sequence including an
      RGD targeting agent

<400> SEQUENCE: 36

```
Arg Gly Asp Ser
1
```

<210> SEQ ID NO 37
<211> LENGTH: 4
<212> TYPE: PRT
<213> ORGANISM: Artificial Sequence
<220> FEATURE:
<223> OTHER INFORMATION: hydrophilic amino acid sequence including an
      RGD targeting agent

<400> SEQUENCE: 37

```
Gly Arg Gly Asp
1
```

<210> SEQ ID NO 38
<211> LENGTH: 5
<212> TYPE: PRT
<213> ORGANISM: Artificial Sequence
<220> FEATURE:

<223> OTHER INFORMATION: hydrophilic amino acid sequence including an
      RGD targeting agent

<400> SEQUENCE: 38

Gly Arg Gly Asp Ser
1               5

<210> SEQ ID NO 39
<211> LENGTH: 6
<212> TYPE: PRT
<213> ORGANISM: Artificial Sequence
<220> FEATURE:
<223> OTHER INFORMATION: hydrophilic amino acid sequence including an
      RGD targeting agent

<400> SEQUENCE: 39

Gly Arg Gly Asp Ser Pro
1               5

<210> SEQ ID NO 40
<211> LENGTH: 7
<212> TYPE: PRT
<213> ORGANISM: Artificial Sequence
<220> FEATURE:
<223> OTHER INFORMATION: hydrophilic amino acid sequence including an
      RGD targeting agent

<400> SEQUENCE: 40

Gly Arg Gly Asp Ser Pro Lys
1               5

<210> SEQ ID NO 41
<211> LENGTH: 6
<212> TYPE: PRT
<213> ORGANISM: Artificial Sequence
<220> FEATURE:
<223> OTHER INFORMATION: hydrophilic amino acid sequence including an
      RGD targeting agent

<400> SEQUENCE: 41

Gly Arg Gly Asp Asn Pro
1               5

<210> SEQ ID NO 42
<211> LENGTH: 6
<212> TYPE: PRT
<213> ORGANISM: Artificial Sequence
<220> FEATURE:
<223> OTHER INFORMATION: hydrophilic amino acid sequence including an
      RGD targeting agent

<400> SEQUENCE: 42

Gly Arg Gly Asp Thr Pro
1               5

<210> SEQ ID NO 43
<211> LENGTH: 9
<212> TYPE: PRT
<213> ORGANISM: Artificial Sequence
<220> FEATURE:
<223> OTHER INFORMATION: targeting motif

<400> SEQUENCE: 43

Cys Arg Lys Arg Leu Asp Arg Asn Cys
1               5

<210> SEQ ID NO 44

-continued

```
<211> LENGTH: 9
<212> TYPE: PRT
<213> ORGANISM: Artificial Sequence
<220> FEATURE:
<223> OTHER INFORMATION: targeting motif

<400> SEQUENCE: 44

Cys Arg Lys Arg Leu Asp Arg Asn Cys
1               5

<210> SEQ ID NO 45
<211> LENGTH: 11
<212> TYPE: PRT
<213> ORGANISM: Artificial Sequence
<220> FEATURE:
<223> OTHER INFORMATION: targeting motif

<400> SEQUENCE: 45

Asp Phe Glu Glu Ile Pro Glu Glu Tyr Leu Gln
1               5                   10

<210> SEQ ID NO 46
<211> LENGTH: 7
<212> TYPE: PRT
<213> ORGANISM: Artificial Sequence
<220> FEATURE:
<223> OTHER INFORMATION: cross-linking motif

<400> SEQUENCE: 46

Gly Gly Gly Cys Cys Gly Gly
1               5

<210> SEQ ID NO 47
<211> LENGTH: 15
<212> TYPE: PRT
<213> ORGANISM: Artificial Sequence
<220> FEATURE:
<223> OTHER INFORMATION: amphiphilic peptide
<220> FEATURE:
<221> NAME/KEY: X
<222> LOCATION: (1)..(3)
<223> OTHER INFORMATION: Each X is pentafluoro phenylalanine
      (2,3,4,5,6-pentafluoro-L-phenylalanine).

<400> SEQUENCE: 47

Xaa Xaa Xaa Gly Gly Gly Cys Cys Gly Gly Lys Gly Arg Gly Asp
1               5                   10                  15

<210> SEQ ID NO 48
<211> LENGTH: 5
<212> TYPE: PRT
<213> ORGANISM: Artificial Sequence
<220> FEATURE:
<223> OTHER INFORMATION: C-terminally amidated hydrophilic amino acid
      sequence which contains targeting motif RGD
<220> FEATURE:
<221> NAME/KEY: AMIDATION
<222> LOCATION: (5)..(5)

<400> SEQUENCE: 48

Lys Gly Arg Gly Asp
1               5

<210> SEQ ID NO 49
<211> LENGTH: 15
<212> TYPE: PRT
<213> ORGANISM: Artificial Sequence
<220> FEATURE:
<223> OTHER INFORMATION: amphiphilic peptide
```

```
<220> FEATURE:
<221> NAME/KEY: X
<222> LOCATION: (1)..(3)
<223> OTHER INFORMATION: Each X is pentafluoro phenylalanine
      (2,3,4,5,6-pentafluoro-L-phenylalanine).
<220> FEATURE:
<221> NAME/KEY: Amidation
<222> LOCATION: (15)..(15)

<400> SEQUENCE: 49

Xaa Xaa Xaa Gly Gly Gly Cys Cys Gly Gly Lys Gly Arg Gly Asp
1               5                   10                  15

<210> SEQ ID NO 50
<211> LENGTH: 6
<212> TYPE: PRT
<213> ORGANISM: Artificial Sequence
<220> FEATURE:
<223> OTHER INFORMATION: hydrophilic amino acid sequence including a
      targeting agent

<400> SEQUENCE: 50

Cys Arg Gly Arg Arg Thr
1               5
```

ULTRASOUND-SENSITIVE PEPTIDE PARTICLES FOR SPATIALLY RESOLVED MOLECULE DELIVERY

REFERENCE TO RELATED APPLICATION

This application claims priority from U.S. Provisional Patent Application Ser. No. 62/538,116, filed Jul. 28, 2017, the entire content of which is incorporated herein by reference.

STATEMENT REGARDING FEDERALLY SPONSORED RESEARCH OR DEVELOPMENT

This invention was made with government support under Grant No. BC011314 awarded by the National Institutes of Health. The Government has certain rights in the invention.

FIELD OF THE INVENTION

The present invention is directed to drug delivery vehicles, and more specifically to a fluorous phase-directed peptide assembly capable of ultrasound-triggered cellular delivery.

BACKGROUND OF THE INVENTION

Protein and nucleic-acid based agents are some of the most potent therapeutic tools used in precision medicine. They deliver biologically active cargo to target cells and are revolutionizing the treatment of various human diseases, including cancer, autoimmune disorders and diabetes. However, therapeutic utility of these biomacromolecules is limited by their ineffective distribution to diseased tissues, poor stability in physiologic environments, and toxic side effects. Importantly, many large biomolecules are unable to penetrate into cells and, therefore, existing biotherapeutics have been restricted to disease targets displayed on the cell surface. Due to the large size, traditional biocarriers rely on endocytic transport processes to enter diseased cells, ultimately leading to degradation of delivered biologics in the harsh endosomal environment. The cell-targeted biocarriers also require multi-step harsh physical and chemical formulation methods that ultimately render biological cargo inactive.

Dynamic peptide assemblies can be formed as a result of a spontaneous self-sorting and assembly process. The architecture and behavior of these self-assembled peptide structures can be controlled by modulating the physicochemical properties of the building blocks, environmental conditions, or assembly kinetics. This has resulted in a wide variety of ordered peptide arrangements including sheets, fibrils, and tubes, which are playing increasingly important roles in the formation of biomaterials and biomedical devices. While various peptide assemblies have been described in the literature, there have been no reports of using these peptide assemblies as drug delivery vehicles for delivering, for example, protein and nucleic acid-based therapeutic agents into cells.

On the contrary, currently known protein delivery vehicles transport proteins intracellularly using the endocytic pathway whereby the vehicle must undergo endosomal escape for successful cytoplasmic delivery. Endosomal escape requires proton pumping into the endosome which lowers the pH and can lead to protein denaturation. A delivery vehicle capable of direct intracellular delivery, bypassing the endocytic pathway, is favorable for effective protein therapy. In light of the valuable therapeutic potential of protein and nucleic-acid based therapeutic compounds, effective compositions and methods to introduce such compounds into cells is needed in the art. The present invention is believed to be an answer to that need.

SUMMARY OF THE INVENTION

In an embodiment, provided is an amphiphilic peptide represented by Formula (I):

HB-CL-HP     (I)

wherein in Formula (I),
HB is a fluorinated hydrophobic block,
CL is a cross-linking motif; and
HP is a hydrophilic amino acid sequence.

In another embodiment, an amphiphilic peptide represented by Formula (I) is provided:

HB-CL-HP     (I)

wherein HB is a fluorinated hydrophobic amino acid sequence comprising from 1 to 10 hydrophobic amino acid residues, wherein at least one of the hydrophobic amino acid residues is fluorinated; CL is a cross-linking motif comprising from about 1 to about 10 amino acid residues; and HP is a hydrophilic amino acid sequence comprising from 3 to 15 hydrophilic amino acids; wherein the amphiphilic peptide comprises from 10 to 30 total amino acid residues and wherein the amphiphilic peptide is capable of assembling at the surface of a perfluorocarbon liquid to form a peptisome. According to embodiments, the amphiphilic peptide does not include lipids.

In another embodiment, provided is a peptisome containing a perfluorocarbon liquid core and a therapeutically active agent dispersed in the perfluorocarbon liquid. The assembly further includes a plurality of amphiphilic peptide molecules surrounding the perfluorocarbon liquid core, wherein the amphiphilic peptide is represented by the above Formula (I).

In still another embodiment, provided is a method of delivering a therapeutically active agent to a target cell. According to the method, a composition including the above peptisome loaded with the therapeutically active agent is provided. The composition is then administered to a patient, and an ultrasound radiation is applied to release the therapeutically active entity from the peptisome.

In yet another embodiment, provided is a method of treating cancer in a patient, wherein the method includes the steps of administering the above peptisome to the patient, and applying ultrasound radiation to a diseased tissue of the patient to release the therapeutically active entity from the peptisome.

Amphiphilic peptides represented by Formula (I): HB-CL-HP (I) are provided according to embodiments, wherein HB is a fluorinated hydrophobic block, CL is a cross-linking motif; and HP is a hydrophilic amino acid sequence, wherein said amphiphilic peptide comprises from 5 to 30 total amino acid residues and wherein said amphiphilic peptide is capable of assembling at the surface of a perfluorocarbon liquid such that HB, the fluorinated hydrophobic block interpolates with the perfluorocarbon liquid and the hydrophilic amino acid sequence extends away from the perfluorocarbon liquid, to form a peptisome or nanopeptisome. According to embodiments, HB of Formula (I) includes one pentafluoro-phenylalanine residue at a terminal thereof, one pentafluoro-phenylalanine residue at each terminal of HB, two, three, four or five consecutively connected pentafluoro-phenylalanine residues at a terminal of HB or two, three, four or five consecutively connected pentafluoro-phenylalanine residues at each terminal of HB. According to preferred embodiments, the pentafluoro-phenylalanine residue is a residue of 2,3,4,5,6-pentafluoro-L-phenylalanine. According to embodiments, the amphiphilic peptides do not include lipids.

Amphiphilic peptides represented by Formula (II) or Formula (III): HB-CL-HP (II), HB-CL-HP—NH$_2$ (III) are provided according to embodiments, wherein HB is a fluorinated hydrophobic amino acid sequence containing at least one fluorinated amino acid residue; CL is a cross-linking motif; and HP is a hydrophilic amino acid sequence. According to embodiments, HB of Formula (II) and/or (III) includes one pentafluoro-phenylalanine residue at a terminal thereof, one pentafluoro-phenylalanine residue at each terminal of HB, two, three, four or five consecutively connected pentafluoro-phenylalanine residues at a terminal of HB or two, three, four or five consecutively connected pentafluoro-phenylalanine residues at each terminal of HB. According to preferred embodiments, the pentafluoro-phenylalanine residue is a residue of 2,3,4,5,6-pentafluoro-L-phenylalanine. According to embodiments, the amphiphilic peptides do not include lipids.

According to embodiments, the hydrophilic amino acid sequence HP includes lysine, glycine, arginine, aspartic acid, or any combination of two or more thereof. According to embodiments, the hydrophilic amino acid sequence HP includes the amino acid sequence KGRGD (SEQ ID NO: 35). According to embodiments, the cross-linking motif CL includes at least two cross-linkable moieties. According to embodiments, the cross-linking motif CL includes at least two cysteines. According to embodiments, the cross-linking motif CL includes GGGCCGG (SEQ ID NO: 46). According to embodiments, the amphiphilic peptides do not include lipids.

According to embodiments, the hydrophilic amino acid sequence HP includes a conserved targeting motif. According to embodiments, the hydrophilic amino acid sequence HP includes a conserved targeting motif selected from the group consisting of: HGK, RGD, KAR, RSR, KAA, RGRR (SEQ ID NO:1), RGRRS (SEQ ID NO:2), YQLDV (SEQ ID NO:3), EYQ, RPM, PSP, VGVA (SEQ ID NO:4), NGR, CRKRLDRNC (SEQ ID NO:43), EFEEFEIDEEEK (SEQ ID NO:44), and DFEEIPEEYLQ (SEQ ID NO:45). According to embodiments, the hydrophilic amino acid sequence HP includes a hydrophilic amino acid sequence selected from the group consisting of: GHGKHKNK (SEQ ID NO:5), CRGDKGPDC (SEQ ID NO:6), CKGAKAR (SEQ ID NO:7). CRVSRQNKC (SEQ ID NO:8), CGGERGKSC (SEQ ID NO:9), CRSRKG (SEQ ID NO:10), CKAAKN (SEQ ID NO:11), CRGRRST (SEQ ID NO:12), CRGRRT (SEQ ID NO:50), CEYQLDVE (SEQ ID NO:13), TVRTSAD (SEQ ID NO:14), PIEDRPM (SEQ ID NO:15), ALRDRPM (SEQ ID NO:16), PEKFRPM (SEQ ID NO:17), IKVGKLQ (SEQ ID NO:18), SVSVGMKPSPRP (SEQ ID NO:19), VPEQRPM (SEQ ID NO:20), CAKIDPELC (SEQ ID NO:21), CSNIDARAC (SEQ ID NO:22), RLQLKL (SEQ ID NO:23), PMMRQRPM (SEQ ID NO:24), AKATCPA (SEQ ID NO:25), QPPMEYS (SEQ ID NO:26), SISSLTD (SEQ ID NO:27), FRVGVADV (SEQ ID NO:28), CNGRCVSGCAGRC (SEQ ID NO:29), NWGDRIL (SEQ ID NO:30), CVSNPRWKC (SEQ ID NO:31), CDCRGDCFC (SEQ ID NO:32), YSAYPDSVPMMS (SEQ ID NO:33), and PLASRPM (SEQ ID NO:34). According to embodiments, the hydrophilic amino acid sequence HP includes a hydrophilic amino acid sequence selected from the group consisting of: KGRGD (SEQ ID NO:35), RGDS (SEQ ID NO:36), GRGD (SEQ ID NO:37), GRGDS (SEQ ID NO:38), GRGDSP (SEQ ID NO:39), GRGDSPK (SEQ ID NO:40), GRGDNP (SEQ ID NO:41), and GRGDTP (SEQ ID NO:42).

Amphiphilic peptides represented by Formula (IV) or Formula (V): $F_FF_FF_F$GGGCCGGKGRGD (IV) (SEQ ID NO:47), $F_FF_FF_F$GGGCCGGKGRGD-NH$_2$ (V) (SEQ ID NO:49) are provided according to embodiments, wherein $F_F$ is pentafluoro-phenylalanine (2,3,4,5,6-pentafluoro-L-phenylalanine), G is glycine, C is cysteine, K is lysine, G is glycine, R is arginine, and D is aspartic acid. $F_FF_FF_F$GGGCCGGKGRGD-NH$_2$ is C-terminally amidated. According to embodiments, the amphiphilic peptides do not include lipids.

Amphiphilic peptides represented by Formula (I): HB-CL-HP (I) are provided according to embodiments, wherein HB is a fluorinated hydrophobic amino acid sequence comprising from 1 to 10 hydrophobic amino acid residues wherein at least one of the hydrophobic amino acid residues is fluorinated; CL is a cross-linking motif comprising from about 1 to about 10 amino acid residues; and HP is a hydrophilic amino acid sequence comprising from 3 to 15 hydrophilic amino acids; wherein said amphiphilic peptide comprises from 10 to 30 total amino acid residues and wherein said amphiphilic peptide is capable of assembling at the surface of a perfluorocarbon liquid such that HB, the fluorinated hydrophobic amino acid sequence interpolates with the perfluorocarbon liquid and the hydrophilic amino acid sequence HP extends away from the perfluorocarbon liquid, to form a peptisome or nanopeptisome. According to embodiments, the amphiphilic peptides do not include lipids.

Amphiphilic peptides represented by Formula (I): HB-CL-HP (1) are provided according to embodiments wherein HB includes a fluorinated hydrophobic polymer, wherein the amphiphilic peptide has a molecular weight in the range of about 2000-5000 daltons, wherein the amphiphilic peptide includes at least five amino acid residues, and a total number of no more than 30 amino acid residues, wherein at least two of the amino acid residues are consecutively linked to each other in a chain by a peptide bond. According to embodiments, the amphiphilic peptides do not include lipids.

Peptisomes are provided according to embodiments, the peptisomes including: a perfluorocarbon liquid core comprising a perfluorocarbon liquid and a cargo dispersed in the perfluorocarbon liquid; and a plurality of amphiphilic peptides according to any of Formulas (I), (II), (III), (IV), or (V) surrounding the perfluorocarbon liquid core, wherein the amphiphilic peptides are oriented such that the fluorinated hydrophobic block HB of each of the amphiphilic peptides are interpolated into the perfluorocarbon liquid of the perfluorocarbon liquid core, the amphiphilic peptides are cross-linked to each other through the cross-linking motif CL, and hydrophilic amino acid sequences HP extend away from the perfluorocarbon liquid core. According to embodiments, the peptisomes do not include lipids.

According to embodiments, the peptisomes have an average diameter in the range from about 1 micron to about 5 microns. According to embodiments, the peptisomes are nanopeptisomes having an average diameter in the range from about 250 nanometers to about 1000 nanometers. According to embodiments, the peptisomes are nanopeptisomes having an average diameter in the range from about 250 nanometers to about 750 nanometers.

According to embodiments, the peptisomes are characterized by a degree of cross-linking of the amphiphilic peptides which is about 60% or greater as determined by a colorimetric disulfide formation assay, such as described herein.

According to embodiments, the cargo is a protein, a peptide, a nucleic acid, a contrast agent, or a small molecule therapeutic.

According to embodiments, the cargo is a therapeutic agent, a diagnostic agent, a small molecule chemotherapeutic agent, an anti-thrombotic agent, a protein therapeutic agent, a peptide therapeutic agent, a nucleic acid-based agent, or a gene editing agent.

According to embodiments, the peptisomes further include a fluorine-containing cargo solubilizing agent. The fluorine-containing cargo solubilizing agent can be selected from the group consisting of: perfluorooctane ($CF_3(CF_2)_6CF_3$), perfluoroteradecane ($CF_3(CF_2)_{12}CF_3$), trifluoroacetic acid ($CF_3COOH$), pentafluoropropionic acid ($CF_3(CF_2)COOH$), perfluoropentanoic acid ($CF_3(CF_2)_3COOH$), perfluorononanoic acid ($CF_3(CF_2)_7COOH$), perfluorotetradecanoic acid ($CF_3(CF_2)_{12}COOH$), perfluorooctadecanoic acid ($CF_3(CF_2)_{16}COOH$), perfluorocyclohexanecarboxylic acid (($CF_2)_5CFCOOH$), pentafluorophenol (2,3,4,5,6-pentafluorophenol, $C_6F_5OH$), pentafluorobenzaldehyde (2,3,4,5,6-pentafluorobenzaldehyde, $C_6F_5CHO$), or Fmoc-pentafluorophenylalanine (($CF)_5CCH_2C(NHFmoc)COOH$, Fmoc-pentafluoro-L-phenylalanine and/or Fmoc-pentafluoro-D-phenylalanine, and a mixture of any two or more thereof. According to embodiments, the peptisomes do not include lipids.

According to embodiments, the perfluorocarbon liquid comprises a perfluoropentane, the fluorine-containing cargo solubilizing agent comprises perfluorononanoic acid, the plurality of amphiphilic peptides include amphiphilic peptides of formula IV and/or V, and the amphiphilic peptides are crosslinked to each other through the cross-linking motif CL.

Methods of delivering a cargo to a target cell are provided according to embodiments which include the steps of: providing a composition comprising a peptisome described herein; contacting the peptisome and the target cell; and applying ultrasound radiation to activate the peptisome and release the cargo from the peptisome into the target cell. According to embodiments, the cargo is an active agent selected from the group consisting of: a therapeutic agent, a diagnostic agent, a small molecule chemotherapeutic agent, an anti-thrombotic agent, a protein therapeutic agent, a peptide therapeutic agent, a nucleic acid-based agent, and a gene editing agent. The composition optionally further includes a pharmaceutically acceptable excipient selected from the group consisting of a vehicle, an adjuvant, a carrier, and a diluent. In a further option, the cell is in vitro or ex vivo. In a still further option, the cell is a cell of a patient and the method further includes administering the composition to the patient.

According to embodiments, the cell is a cell of a patient, the patient has cancer and the method includes applying ultrasound radiation to a diseased tissue of the patient to release the therapeutically active entity from the peptisome. According to embodiments, the peptisome is a nanopeptisome and the cancer is lung cancer, pancreatic cancer, hepatic cancer, or colorectal cancer and the amphiphilic peptides of the nanopeptisomes include a targeting agent such as HGK to target lung metastases, ROD to target pancreatic cancer, KAR to target pancreatic islet tumors, RSR to target pancreatic islet tumors, KAA to target pancreatic cancer, RGRR (SEQ ID NO:1) to target pancreatic islet carcinoma, RGRRS (SEQ ID NO:2) to target pancreatic islet carcinoma, YQLDV (SEQ ID NO:3) to target pancreatic islet carcinoma, EYQ to target pancreatic islet tumors, RPM to target colorectal cancer, PSP to target lung cancer, VGVA (SEQ ID NO:4) to target pancreatic islet carcinoma, NGR to target hepatic and pancreatic cancers, and RGD to target hepatic and pancreatic cancers.

According to embodiments, the cell is a cell of a patient, the patient has or is suspected of having atherosclerotic plaques or blood clots and the method includes introduction of the peptisomes into the cardiovascular system, such as, but not limited to, by intravenous injection, applying ultrasound radiation to image or therapeutically treat atherosclerotic plaques or blood clots of the patient. According to embodiments, the peptisome is >1000 nm and is used for imaging, or the peptisome is a nanopeptisome having a diameter <1000 nm, such as <750 nm, and the amphiphilic peptides of the nanopeptisomes include a targeting agent such as CRKRLDRNC (SEQ ID NO:43) to target atherosclerotic plaques; EFEEFEIDEEEK (SEQ ID NO:44) to target blood clots; and/or DFEEIPEEYLQ (SEQ ID NO:45) to target blood clots.

These and other aspects of the invention are described in more detail below.

BRIEF DESCRIPTION OF THE DRAWINGS

The above and other aspects and features of the present disclosure will become more apparent in the following detailed description when taken in conjunction with reference to the accompanying drawings, in which.

DETAILED DESCRIPTION OF THE INVENTION

Figure 1:
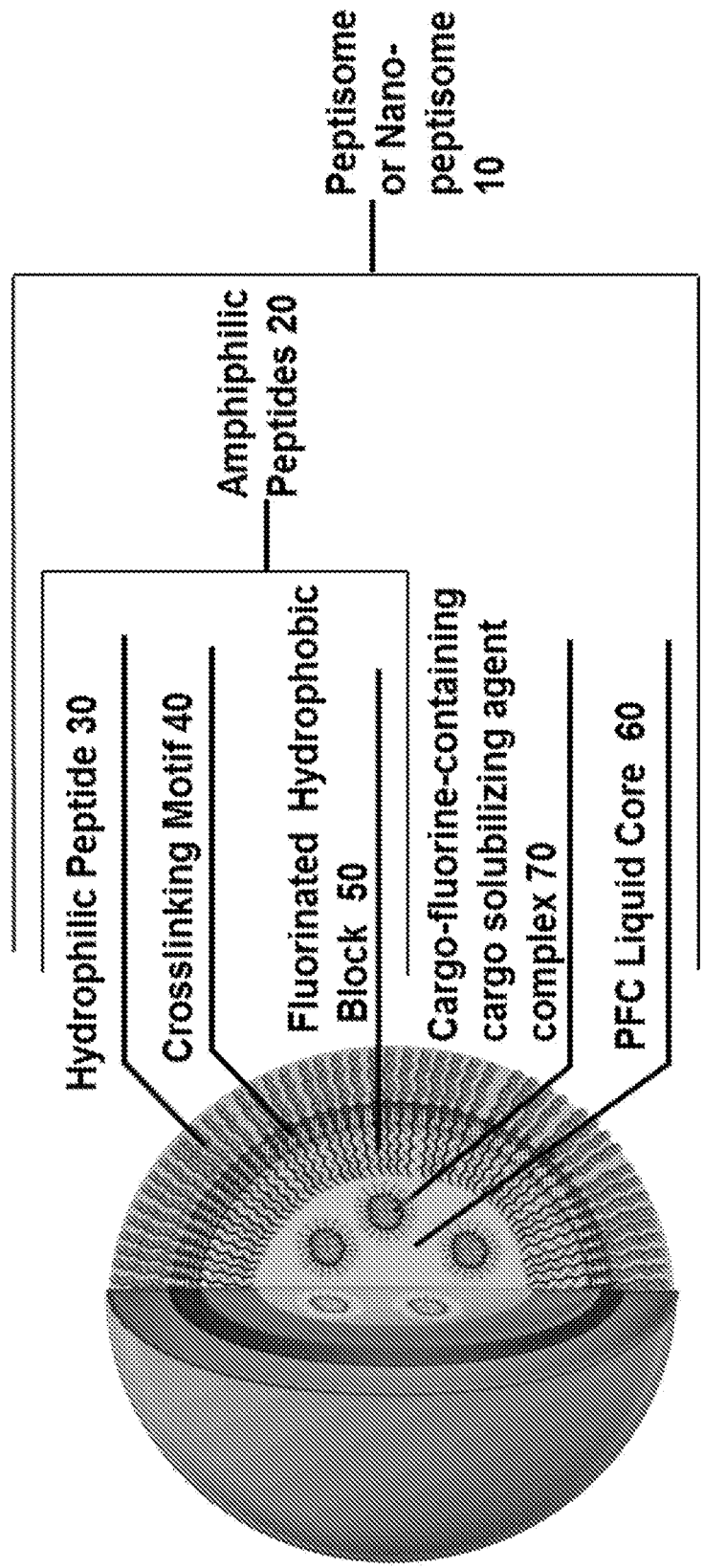
FIG. 1 is a diagram showing structure of peptisomes and nanopeptisomes according to embodiments.

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced items. The term "or" means "and/or". The terms "comprising," "having," "including," and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art of this disclosure.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group.

All compounds are understood to include all possible isotopes of atoms occurring in the compounds. Isotopes include those atoms having the same atomic number but different mass numbers and encompass heavy isotopes and radioactive isotopes. By way of general example, and without limitation, isotopes of hydrogen include tritium and deuterium, and isotopes of carbon include $^{11}$C, $^{13}$C, and $^{14}$C. Accordingly, the compounds disclosed herein may include heavy or radioactive isotopes in the structure of the compounds or as substituents attached thereto. Examples of useful heavy or radioactive isotopes include $^{18}$F, $^{15}$N, $^{18}$O, $^{76}$Br, $^{125}$I and $^{131}$I.

The opened ended term "comprising" includes the intermediate and closed terms "consisting essentially of" and "consisting of."

A dash ("-") that is not between two letters or symbols is used to indicate a point of attachment for a substituent.

"Pharmaceutical compositions" means compositions including at least one active agent, such as a compound or salt of Formula 3, and at least one other substance, such as a carrier. Pharmaceutical compositions meet the U.S. FDA's GMP (good manufacturing practice) standards for human or non-human drugs.

A "patient" means a human or non-human animal in need of medical treatment. Medical treatment can include treatment of an existing condition, such as a disease or disorder or diagnostic treatment. In some embodiments the patient is a human patient.

"Providing" means giving, administering, selling, distributing, transferring (for profit or not), manufacturing, compounding, or dispensing.

"Treatment" or "treating" means providing an active compound to a patient in an amount sufficient to measurably reduce any disease symptom, slow disease progression or cause disease regression. In certain embodiments treatment of the disease may be commenced before the patient presents symptoms of the disease.

A "therapeutically active agent" means a compound which can be used for diagnosis or treatment of a disease. The compounds can be small molecules, peptides, proteins, or other kinds of molecules.

A significant change is any detectable change that is statistically significant in a standard parametric test of statistical significance such as Student's T-test, where p<0.05.

The present invention is directed to novel peptisomes prepared through the templated assembly of amphiphilic peptides at a fluorous-liquid interface containing releasable cargo-fluorine-containing cargo solubilizing agent complexes.

Peptisomes according to embodiments of the present invention have a perfluorocarbon liquid core that phase transitions into a gaseous state upon ultrasound application. When positioned at the cell surface, ultrasound activation serves to deliver cargo encapsulated within the peptisomes into the cytoplasm directly. Thus, proteins, peptides, nucleic acids, small molecule compounds, and other materials, can be encapsulated and directly delivered to the cytoplasm of cells without loss of function. This ultrasound-mediated delivery is ideal for therapeutics due to its spatial and temporal precision.

A typical peptisome is shown at 10 in FIG. 1 including a plurality of amphiphilic peptides 20, wherein the amphiphilic peptides each include a hydrophilic peptide 30, a crosslinking motif 40, and a fluorinated hydrophobic block 50. The fluorinated hydrophobic block of the amphiphilic peptides promotes peptide assembly at the surface of the perfluorocarbon (PFC) liquid core 60, which contains the cargo-fluorine-containing cargo solubilizing agent complexes 70.

Peptisomes having a diameter of from about 250 nm to about 5 microns may be produced. An average diameter of the peptisomes according to embodiments may be from about 1 to about 5 microns, for example, about 1 to about 4 microns, about 1 to about 3 microns, or about 1 to about 2 microns, but is not limited thereto. In an embodiment, the peptisomes are "nanopeptisomes" having an average diameter in the range of about 300 nanometers to 1200 nanometers, about 250 nanometers to about 1000 nanometers, for example, 250 to about 750 nanometers, but is not limited thereto.

The peptisomes contain a perfluorocarbon liquid core that allows for activation of the peptisomes upon application of ultrasound (US) and delivery of a cargo present in the perfluorocarbon liquid core. The term "activation" as used herein to refer to activation of peptisomes upon application of ultrasound refers to phase transition of a perfluorocarbon liquid core into a gaseous state due to ultrasound application.

Figure 2:
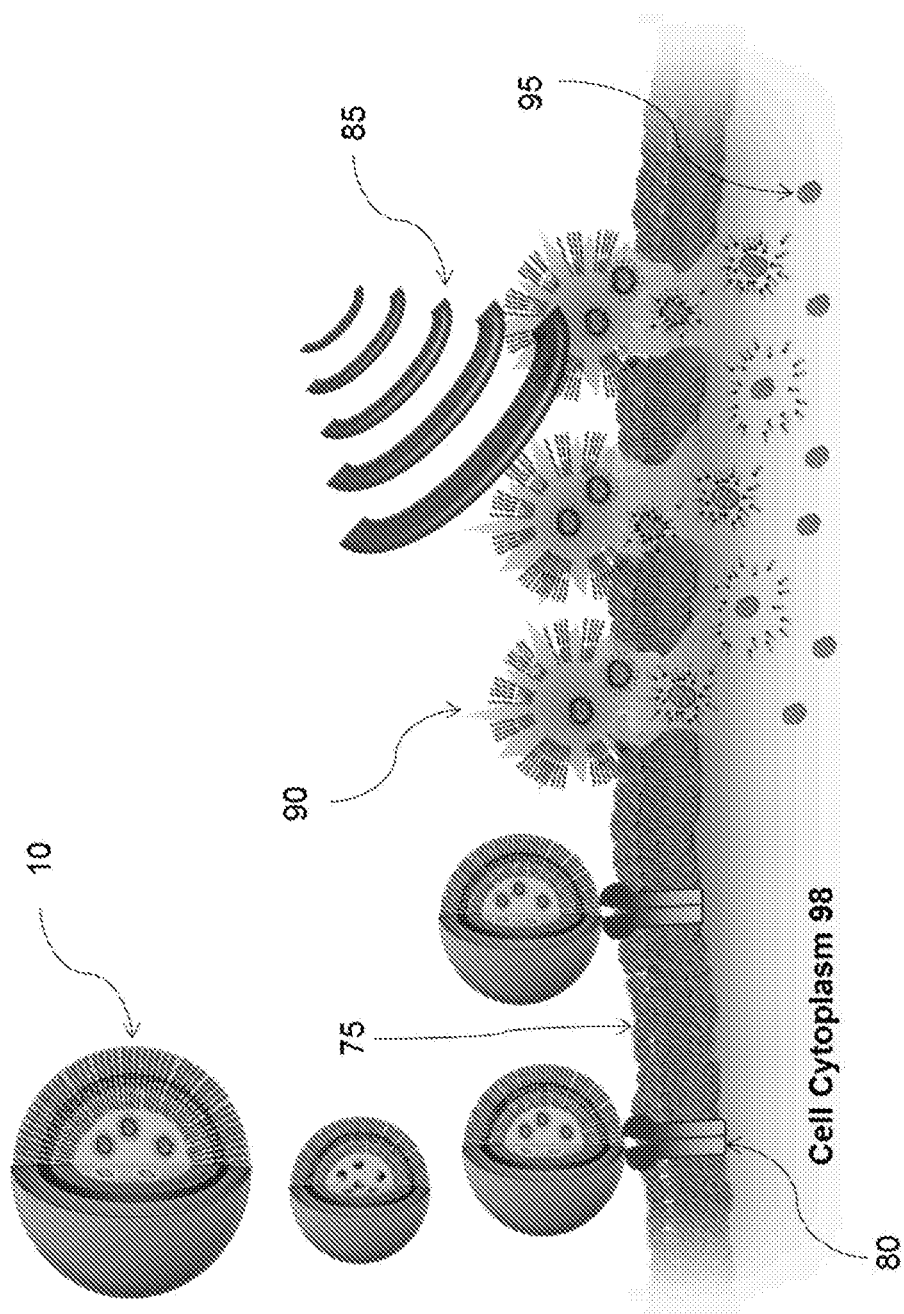
FIG. 2 is a diagram showing target motif-mediated specific binding and ultrasound-mediated delivery of cargo into a targeted cell.

As shown diagrammatically in FIG. 2, peptisome 10 binds to a receptor 80 disposed in or on a cell membrane 75 via specific interaction with the hydrophilic peptide 30 of the amphiphilic peptides of peptisome 10. Application of ultrasound 85 causes acoustic vaporization of the perfluorocarbon liquid core of the peptisomes and leads to the formation of a gaseous core that ultimately swells and ruptures 90 the peptisomes. Subsequent bubble captivation produces a high intensity pressure wave that, when generated at the surface of a cell, transiently permeabilizes the plasma membrane 75, and simultaneously ejects cargo 95 encapsulated in the peptisome into the cell cytoplasm 98. Thus, US-sensitive peptisomes represent a spatially and temporally controlled delivery modality that, as described herein, can deliver a cargo, such as biomacromolecules, directly into the cytoplasm of cells, thereby avoiding endosomal uptake and degradation of the bioactive payload.

Key to the assembly of these peptisomes is a de novo designed amphiphilic peptide, capable of assembling at the surface of a perfluorocarbon liquid.

As noted above, amphiphilic peptides included in peptisomes according to embodiments each include a fluorinated hydrophobic block (HB), a crosslinking motif, and a hydrophilic peptide.

Thus, in one embodiment, an amphiphilic peptide represented by Formula (I) is provided:

HB-CL-HP     (I)

wherein HB is a fluorinated hydrophobic polymer: CL is a cross-linking motif; and HP is a hydrophilic amino acid sequence.

As used herein, the term "amphiphilic peptide" refers to a molecule including a fluorinated hydrophobic polymer; a cross-linking motif; and a hydrophilic amino acid sequence, wherein the amphiphilic peptide has a molecular weight in the range of about 2000-5000 daltons, wherein the amphiphilic peptide includes at least five amino acid residues, and a total number of no more than 30 amino acid residues, wherein at least two of the amino acid residues are consecutively linked to each other in a chain by a peptide bond.

As used herein, the term "fluorinated hydrophobic polymer" refers to a covalently linked chain of monomer residues forming a fluorinated hydrophobic homopolymer or copolymer. The monomeric units which form the fluorinated hydrophobic polymer may each be fluorinated according to embodiments, or some, or one, of the monomeric units is fluorinated such that at least one or more of the monomer residues of the fluorinated hydrophobic polymer is fluorinated.

According to embodiments, the amphiphilic peptide does not include lipids.

According to embodiments, the fluorinated hydrophobic polymer includes a hydrophobic amino acid sequence wherein the amino acids of the hydrophobic amino acid sequence have non-polar side chains, wherein the non-polar side chains do not include a group capable of forming a hydrogen bond with molecules of water, and wherein at least one of the amino acids of the hydrophobic amino acid sequence is fluorinated.

According to embodiments, the fluorinated hydrophobic polymer includes one or more synthetic non-amino acid monomeric units wherein at least one of the monomeric units is fluorinated such that at least one of the monomer residues of the fluorinated hydrophobic polymer is fluorinated. Non-limiting examples of synthetic monomeric units which can be fluorinated and reacted to form a fluorinated hydrophobic polymer include methyl methacrylate; lactic acid, glycolic acid and olefins such as ethylene, propylene, styrene.

As used herein, the term "hydrophobic amino acid sequence" refers to a hydrophobic polymer, a sequence of hydrophobic amino acids having non-polar side chains, wherein the non-polar side chains do not include a group capable of forming a hydrogen bond with molecules of water, or a combination of a hydrophobic polymer and a sequence of hydrophobic amino acids having non-polar side chains. Hydrophobic amino acids may be naturally occurring or non-natural (artificially produced). Examples of the naturally occurring hydrophobic amino acids include, but are not limited to, alanine, valine, leucine, isoleucine, proline, phenylalanine, tryptophan, cysteine, and methionine. Examples of the non-natural hydrophobic amino acids may include D amino acids, as well as specific non-natural amino acids such as selenocysteine, pyrrolysine, and the like.

In the amphiphilic peptide, the fluorinated hydrophobic amino acid sequence may include one to ten fluorinated hydrophobic amino acids consecutively connected by peptide bonds, which may be unsubstituted or substituted with a substituent selected from —F, —Cl, —Br, —I, a $C_1$-$C_{30}$ alkyl group, a $C_2$-$C_{30}$ alkenyl group, a $C_2$-$C_{30}$ alkynyl group, a $C_3$-$C_{30}$ cycloalkyl group, a $C_3$-$C_{30}$ cycloalkenyl group, a $C_6$-$C_{30}$ aryl group, a $C_7$-$C_{30}$ arylalkyl group, but are not limited thereto. For example, the fluorinated hydrophobic amino acid sequence may include one, two, three, four, five, six seven, eight, nine or ten fluorinated hydrophobic amino acids consecutively connected by peptide bonds. Fluorinated hydrophobic amino acids include, for example, fluorinated alanine, fluorinated valine, fluorinated leucine, fluorinated isoleucine, fluorinated proline, fluorinated phenylalanine, fluorinated tryptophan, fluorinated cysteine, fluorinated methionine, fluorinated selenocysteine, and fluorinated pyrrolysine. The fluorinated hydrophobic amino acids can be D or L amino acids and can be fluorinated at any suitable position, typically replacing a hydrogen atom. In an embodiment, the fluorinated hydrophobic amino acid sequence may include pentafluoro-phenylalanine (2,3,4,5,6-pentafluoro-L-phenylalanine and/or 2,3,4,5,6-pentafluoro-D-phenylalanine) at a terminal thereof. In another embodiment, the fluorinated hydrophobic amino acid sequence may include one to ten, such as one, two, three, four, five, six, seven, eight, nine or ten consecutively connected pentafluoro-phenylalanine residues at a terminal thereof.

Fluorinated amino acids can be obtained commercially or synthesized by standard methodologies, such as those described in detail in G. Haufe et al., Amino Acids, September 1996, Volume 11, Issue 3-4, pp 409-424.

A combination of a hydrophobic polymer and a sequence of hydrophobic amino acids having non-polar side chains can be included in the fluorinated hydrophobic polymer wherein at least one of the monomer residues of the fluorinated hydrophobic polymer is fluorinated and/or at least one of the amino acid residues is fluorinated.

As used herein, the term "hydrophilic amino acid sequence" refers to a sequence of hydrophilic amino acids consecutively connected by peptide bonds, wherein the hydrophilic amino acids have a polar side chain, wherein the polar side chain includes a group capable of forming a hydrogen bond with molecules of water. Hydrophilic amino acids may be naturally occurring or non-natural and can be D or L amino acids. Examples of the naturally-occurring hydrophilic amino acids include, but are not limited to, serine, threonine, asparagine, glutamine, histidine and tyrosine. Examples of the non-natural hydrophilic amino acids include amino acids having various heterocyclic groups as a part of the side chain.

In the amphiphilic peptide, the hydrophilic amino acid sequence HP may include three to fifteen hydrophilic amino acids consecutively connected by peptide bonds. For example, the hydrophilic amino acid sequence HP may include one, two, three, four, five, six, seven, eight, nine, ten, eleven, twelve, thirteen, fourteen, or fifteen hydrophilic amino acids consecutively connected by peptide bonds.

In one embodiment, an amphiphilic peptide represented by Formula (II) is provided:

HB-CL-HP            (II)

wherein HB is a fluorinated hydrophobic amino acid sequence; CL is a cross-linking motif; and HP is a hydrophilic amino acid sequence.

In one embodiment, an amphiphilic peptide represented by Formula (III) is provided:

HB-CL-HP-$NH_2$            (III)

wherein HB is a fluorinated hydrophobic amino acid sequence; CL is a cross-linking motif; and HP is a C-terminally amidated hydrophilic amino acid sequence.

In one embodiment, the hydrophilic amino acid sequence includes a targeting agent that interacts with a targeted component of a target cell. The targeted component is at least partially external to the target cell and interaction of the targeting agent and targeted component of the target cells serves to bring peptisomes into proximity with the target cell into which the cargo is to be delivered. The target cells can be cells of any organism, such as, but not limited to, a mammal, bird, fish, or bacterial cell. According to embodiments, the target cell is a human cell or a bacterial cell within a human body.

According to embodiments, the targeting agent includes a minimal targeting motif peptide and optionally includes one or more hydrophilic amino acids attached to the N-terminus or C-terminus of the minimal targeting motif peptide by peptide bonds. Typically, amino acids of the targeting motif peptide are L-amino acids but these may include one or more D-amino acids so long as the targeting motif still correctly mediates binding with the targeted component. The one or more hydrophilic amino acids attached to the N-terminus or C-terminus of the minimal targeting motif peptide by peptide bonds can be D or L amino acids.

According to embodiments, the targeting agent includes a minimal targeting motif peptide selected from: HGK, RGD, KAR, RSR, KAA, RGRR (SEQ ID NO:1), RGRS (SEQ ID NO:2), YQLDV (SEQ ID NO:3), EYQ, RPM, PSP, VGVA (SEQ ID NO:4). NGR, CRKRLDRNC (SEQ ID NO:43) which binds to the IL-4 receptor on atherosclerotic plaques; EFEEFEIDEEEK (SEQ ID NO:44) which binds to thrombin in blood clots; and/or DFEEIPEEYLQ (SEQ ID NO:45) which binds to thrombin in blood clots, and optionally includes one or more hydrophilic amino acids attached to the N-terminus or C-terminus of the minimal targeting motif peptide by peptide bonds.

According to embodiments, the hydrophilic amino acid sequence including a targeting agent includes a hydrophilic amino acid sequence selected from: GHGKHKNK (SEQ ID NO:5), CRGDKGPDC (SEQ ID NO:6), CKGAKAR (SEQ ID NO:7), CRVSRQNKC (SEQ II) NO:8), CGGERGKSC (SEQ ID NO:9), CRSRKG (SEQ ID NO: 10), CKAAKN (SEQ ID NO:11), CRGRRT (SEQ ID NO:50), CRGRRST (SEQ ID NO:12), CEYQLDVE (SEQ ID NO:13), TVRTSAD (SEQ ID NO:14), PIEDRPM (SEQ ID NO:15), ALRDRPM (SEQ ID NO:16), PEKFRPM (SEQ ID NO:17), IKVGKLQ (SEQ ID NO:18), SVSVGMKPSPRP (SEQ ID NO:19), VPEQRPM (SEQ ID NO:20), CAKIDPELC (SEQ ID NO:21), CSNIDARAC (SEQ ID NO:22), RLQLKL (SEQ ID NO:23), PMMRQRPM (SEQ ID NO:24), AKATCPA (SEQ ID NO:25), QPPMEYS (SEQ ID NO:26), SISSLTD (SEQ ID NO:27), FRVGVADV (SEQ ID NO:28), CNGRCVSGCAGRC (SEQ ID NO:29), NWGDRIL (SEQ ID NO:30), CVSNPRWKC (SEQ ID NO:31), CDCRGDCFC (SEQ ID NO:32), YSAYPDSVPMMS (SEQ ID NO:33), and PLASRPM (SEQ ID NO:34).

For example, the hydrophilic amino acid sequence HP may include the amino acid sequence KGRGD (SEQ ID NO:35) as a targeting agent, wherein K is lysine, G is glycine, R is arginine, and D is aspartic acid, which includes minimal targeting motif RGD capable of specific binding to integrins and two hydrophilic amino acids.

Minimal targeting motif RGD alone or with additional hydrophilic amino acids along with the binding affinity to αVβ3 integrin (IC$_{50}$, conc. in nM at which 50% of receptor is bound by ligand): RGD (89±12), RGDS (45±5, SEQ ID NO:36), GRGD (55±7, SEQ ID NO:37), GRGDS (28±3, SEQ ID NO:38), GRGDSP (13.7±0.3, SEQ ID NO:39), GRGDSPK (12.2±0.1, SEQ ID NO:40), GRGDNP (45±12, SEQ ID NO:41), and GRGDTP (28±5, SEQ ID NO:42x). Thus, according to embodiments, the hydrophilic amino acid sequence HP includes, RGD, KGRGD (SEQ ID NO:35), RGDS (SEQ ID NO:36), GRGD (SEQ ID NO:37), GRGDS (SEQ ID NO:38), GRGDSP (SEQ ID NO:39), GRGDSPK (SEQ ID NO:40), GRGDNP (SEQ ID NO:41), or GRGDTP (SEQ ID NO:42).

According to embodiments, the targeting agent of the hydrophilic amino acid sequence interacts with a targeted component of a target cancer cell.

As will be appreciated by those of skill in the art, some targeting agents are recognized by both normal cells and pathological cells. In such cases, higher expression of the targeted component is typically present in the pathological cells, such as cancer cells. For example, integrins are expressed by a wide variety of normal cells. However, integrins are expressed at much higher levels in cancer cells.

Examples of minimal targeting motifs suitable for inclusion in cancer targeting agents, tumors which express targeted components which specifically bind the minimal targeting motif, and examples of hydrophilic amino acid sequences including a targeting motif which can be included in amphiphilic peptides according to embodiments, are shown in Table 1.

TABLE 1

| Target-tumor | Minimal Targeting Motif | Example hydrophilic amino acid sequence including a targeting motif |
|---|---|---|
| Lung metastasis | HGK | GHGKHKNK (SEQ ID NO: 5) |
| Pancreatic cancer + | RGD | CRGDKGPDC (SEQ ID NO: 6) |
| Pancreatic islet tumors | KAR | CKGAKAR (SEQ ID NO: 7) |
| Lung cancer | – | CRVSRQNKC (SEQ ID NO: 8) |
| Lung cancer | – | CGGERGKSC (SEQ ID NO: 9) |
| Pancreatic islet tumors | RSR | CRSRKG (SEQ ID NO: 10) |
| Pancreatic cancer | KAA | CKAAKN (SEQ ID NO: 11) |
| Pancreatic islet carcinoma | RGRR (SEQ ID NO: 1) | CRGRRT (SEQ ID NO: 50) |
| Pancreatic islet carcinoma | RGRRS (SEQ ID NO: 2) | CRGRRST (SEQ ID NO: 12) |
| Pancreatic islet carcinoma | YQLDV (SEQ ID NO: 3) | CEYQLDVE (SEQ ID NO: 13) |
| Pancreatic islet tumors | EYQ | CEYQLDVE (SEQ ID NO: 13) |
| Lung cancer | | TVRTSAD (SEQ ID NO: 14) |
| Colorectal cancer | RPM | PIEDRPM (SEQ ID NO: 15) |
| Colorectal cancer | RPM | PIDERPM (SEQ ID NO: 15) |
| Colorectal cancer | RPM | ALRDRPM (SEQ ID NO: 16) |
| Colorectal cancer | RPM | PEKFRPM (SEQ ID NO: 17) |
| Lung cancer | | IKVGKLQ (SEQ ID NO: 18) |
| Lung cancer - tumor vessel | PSP | SVSVGMKPSPRP (SEQ ID NO: 19) |
| Colorectal cancer | RPM | VPEQRPM (SEQ ID NO: 20) |
| Lung cancer | – | CAKIDPELC (SEQ ID NO: 21) |
| Lung cancer | – | CSNIDARAC (SEQ ID NO: 22) |
| Lung metastasis | – | RLQLKL (SEQ ID NO: 23) |
| Colorectal cancer | RPM | PMMRQRPM (SEQ ID NO: 24) |
| Lung cancer | | AKATCPA (SEQ ID NO: 25) |

TABLE 1-continued

| Target-tumor | Minimal Targeting Motif | Example hydrophilic amino acid sequence including a targeting motif |
|---|---|---|
| Colorectal cancer | — | QPPMEYS (SEQ ID NO: 26) |
| Lung cancer | | SISSLTD (SEQ ID NO: 27) |
| Pancreatic isle carcinoma | VGVA (SEQ ID NO: 4) | FRVGVADV (SEQ ID NO: 28) |
| Hepatic and pancreatic | NGR | CNGRCVSGCAGRC (SEQ ID NO: 29) |
| Lung cancer | | NWGDRIL (SEQ ID NO: 30) |
| Pancreatic islet tumors | — | CVSNPRWKC (SEQ ID NO: 31) |
| Hepatic and pancreatic | RGD | CDCRGDCFC (SEQ ID NO: 32) |
| Pancreatic islet tumors | — | YSAYPDSVPMMS (SEQ ID NO: 33) |
| Colorectal cancer | RPM | PLASRPM (SEQ ID NO: 34) |

As used herein, the phrase "cross-linking motif" refers to an amino acid sequence that includes, at any position in the sequence, at least two amino acid residues each capable of cross-linking with a corresponding amino acid residue capable of cross-linking and present in another amphiphilic peptide.

The at least two amino acid residues capable of cross-linking with a corresponding amino acid residue in the crosslinking motif of another amphiphilic peptide can be a naturally occurring amino acids and/or a non-naturally occurring amino acids.

Naturally occurring amino acids capable of crosslinking with a corresponding amino acid residue include cysteine.

An amino acid may be functionalized to such that it is a non-naturally occurring amino acid to provide the ability to bind to a naturally occurring or non-naturally occurring amino acid in the crosslinking motif of another amphiphilic peptide.

In exemplary embodiments, the cross-linking motif may include cross linking moieties such as sulfhydryl cross-linkers, UV cross-linkers, aza-benzenes, photosensitive crosslinkers such as azides or benzophenones, nitriles, pH sensitive cross-linkers, or enzymatic cross-linkers.

In an embodiment, the cross-linking motif may include cysteine, and may optionally further include glycine. For example, in one preferred embodiment, the cross-linking motif CL may include GGGCCGG (SEQ ID NO:46), wherein G is glycine and C is cysteine. The crosslinking motif CL may comprise from 1 to about 10 amino acid residues.

In the peptisomes, the amphiphilic peptide molecules are oriented in such a way that groups HB of the peptide are located at a surface of the perfluorocarbon liquid of the perfluorocarbon liquid core, wherein the amphiphilic peptide molecules are bonded intramolecularly. For example, when the cross-linking motif of the amphiphilic peptide includes a cysteine residue, the amphiphilic peptide molecules may be cross-linked via disulfide cross-linking groups (—S—S—). When the cross-linking motif of the amphiphilic peptide includes two or more cysteine residues, the two or more cysteine residues may be intramolecularly connected via disulfide cross-linking groups (—S—S—).

A degree of cross-linking of the amphiphilic peptide molecules may be about 50% or greater, for example, about 55% or greater, about 60% or greater, about 65% or greater, about 70% or greater, about 75% or greater, about 80% or greater, about 85% or greater, about 90% or greater, or about 95% or greater. The degree of crosslinking may be measured using a colorimetric disulfide formation assay (described in detail below).

The amphiphilic peptide, according to an embodiment, may include 5 to 30 amino acids and has a molecular weight in the range of about 2000-5000 daltons. For example, the amphiphilic peptide may include 5, 6, 7, 8, 9, 10, 11, 12, 13, 14, 15, 16, 17, 18, 19, 20, 21, 22, 23, 24, 25, 26, 27, 28, 29, or 30 amino acids wherein the amphiphilic peptide has a molecular weight in the range of about 2000-5000 daltons.

In an embodiment, the amphiphilic peptide has Formula (IV):

(IV)
(SEQ ID NO: 47)

wherein $F_F$ is pentafluoro-phenylalanine (2,3,4,5,6-pentafluoro-L-phenylalanine), G is glycine, C is cysteine, K is lysine, G is glycine, R is arginine, and D is aspartic acid. In Formula (IV), $F_F F_F F_F$ is a hydrophobic block HB, GGGCCGG (SEQ ID NO:46) is a cross-linking motif CL, and KGRGD (SEQ ID NO:35) is a hydrophilic amino acid sequence HP, which contains targeting motif RGD.

In an embodiment, the amphiphilic peptide has Formula (V):

(V)
(SEQ ID NO: 49)
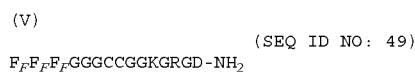

wherein $F_F$ is pentafluoro-phenylalanine, G is glycine, C is cysteine, K is lysine, G is glycine, R is arginine, and D is aspartic acid, and the amphiphilic peptide is C-terminally amidated. In Formula (TV), $F_F F_F F_F$ is a hydrophobic block HB, GGGCCGG (SEQ ID NO:46) is a cross-linking motif CL, and KGRGD-NH$_2$ (SEQ ID NO:48) is a C-terminally amidated hydrophilic amino acid sequence HP, which contains targeting motif RGD.

Amphiphilic peptides can be synthesized using techniques known to one of ordinary skill in the art, such as, but not limited to, solid-phase synthesis, recombinant methodologies, polymerization, and conjugation methods.

Advantageously, amphiphilic peptides according to embodiments of the present invention may include highly fluorinated amino acid residues and such sequences may be chemically synthesized in high yield and purity using standard solid-phase techniques known to one of ordinary skill in the art.

The amphiphilic peptides of all of Formulas (I), (II), (III), (IV), and (V) are capable of assembling at the surface of a perfluorocarbon liquid and assemble into a layer to form a peptisome.

Amphiphilic peptides (IV) and (V) contain three pentafluoro-phenylalanine ($F_F$) residues at the N-terminus which promote interpolation and assembly of the peptide at the perfluorocarbon liquid interface. C-terminal to this fluorous domain is a cysteine-containing crosslinking motif (GGGCCGG, SEQ ID NO:46) designed to undergo disulfide cross-linking to an adjacent amphiphilic peptide in order to stabilize the peptide corona after templated assembly. Incorporation of a bioactive hydrophilic sequence at the peptide's C-terminus ultimately leads to its multivalent display at the surface of the assembled particle. The amphiphilic peptides of Formulas (IV) and (V) include the sequence KGRGD (SEQ ID NO:35) to enable cell-surface localization of peptisomes including the amphiphilic peptides of Formulas (IV) and (V) mediated by binding of the targeting motif RGD with extracellular integrins.

As noted above, the peptisomes contain a perfluorocarbon (PFC) liquid core that allows for activation of the particle upon application of ultrasound (US) and delivery of a cargo present in the perfluorocarbon liquid core.

As used herein, the term "perfluorocarbon" refers to a hydrocarbon in which, all or a substantial portion of hydrogen atoms in C—H bonds are replaced with fluorine atoms, producing C—F bonds. The degree of replacement of hydrogen atoms with fluorine atoms may vary, and may be 100%, 99% or greater, 98% or greater, 97% or greater, 96% or greater, 95% or greater, 90% or greater, 85% or greater, 80% or greater, 75% or greater, or 70% or greater. In another embodiment, the degree of replacement of hydrogen atoms with fluorine atoms may be 100%, 99.9% or greater, 99.8% or greater, 99.7% or greater, 99.6% or greater, 99.5% or greater, 99.4% or greater, 99.3% or greater, 99.2% or greater, or 99.1% or greater. The perfluorocarbon liquid may be a perfluorobutane, a perfluoropentane, a perfluorohexane, an octafluoropropane, but is not limited thereto. The perfluorocarbon liquid may be a perfluoropentane, for example, perfluoro-n-pentane (PFP) or perfluoro-iso-pentane. The perfluorocarbon liquid may be a perfluorohexane, for example, perfluoro-n-hexane (PFH), perfluoro-iso-hexane, or perfluoro-sec-hexane. As used herein, the term "perfluorocarbon liquid" generally refers to a perfluorocarbon as defined above, which is present in a liquid state at ambient temperature of about 25° C. The perfluorocarbon liquid may have a boiling point of about 45° C. or lower, for example, about 40° C. or lower, about 35° C. or lower, or about 30° C. or lower. While not wishing to be bound to any theory, it is understood that the higher the boiling point of the perfluorocarbon liquid, the greater ultrasound intensity should be utilized to acoustically vaporize the perfluorocarbon liquid core of the peptisomes which leads to the formation of a gaseous core that ultimately swells and ruptures the peptisomes. Accordingly, when the boiling point of the perfluorocarbon liquid is too high, for example, greater than 45° C., cells may be damaged by the application of the ultrasound.

On the other hand, the intensity of the ultrasound should be sufficient to release the cargo from the peptisomes into the cells. To ensure, however, that no cell damage occurs, the intensity of the ultrasound should not be greater than 1.0 watts per square centimeter (W/cm$^2$), and its mechanical index (MI) should be maintained below 1.9. Ultrasound systems for in vitro and in vivo application are commercially available, such as Toshiba Medical Systems Aplio500 and GE Healthcare Logiq E9, and these and other such systems can be used according to the manufacturers specifications to administer ultrasound to a patient, or to isolated cells to image peptisomes and/or deliver a cargo to targeted cells or regions such as atherosclerotic plaques or blood clots.

The cargo included in peptisomes to be delivered into a cell may include a therapeutically active agent, for example, a small molecule therapeutic agent, a protein therapeutic agent, a peptide therapeutic agent, a nucleic acid-based agent, such as RNA, DNA, an miRNA molecule, an siRNA molecule, an shRNA molecule, a dsRNA molecule, an antisense molecule, a ribozyme, a polynucleotide encoding an miRNA, siRNA, shRNA, dsRNA; or a combination of any two or more thereof, a gene editing tool (such as clustered regularly interspaced short palindromic repeats "CRISPR"), but is not limited thereto. The therapeutically active agent may include a radioisotope.

Such therapeutically active agents include, but are not limited to, an anti-thrombotic agent, antibiotics, antivirals, antineoplastic agents, analgesics, antipyretics, antidepressants, antipsychotics, anti-cancer agents, antihistamines, anti-osteoporosis agents, anti-osteonecrosis agents, antiinflammatory agents, anxiolytics, chemotherapeutic agents, diuretics, growth factors, hormones, non-steroidal anti-inflammatory agents, steroids and vasoactive agents.

The perfluorocarbon liquid core may further include a bioimaging agent, for example, a photoacoustic dye (such as indocyanine green "ICG", Cyanine 7 "Cy7", or dimethyl {4-[1,5,5-tris(4-dimethylaminophenyl)-2,4-pentadienylidene]-2,5-cyclohexadien-1-ylidene}ammonium perchlorate "IR800"), a fluorescent dye or protein (such as green fluorescent protein "GFP", fluorescein, rhodamine, a cyanine dye), and a magnetic resonance imaging "MRI" contrast agent (such as iron oxide or gadolinium), a radiotracer, but is not limited thereto.

According to embodiments, the perfluorocarbon liquid core includes about $1\times10^3$ to about $5\times10^9$ molecules, such as $1\times10^4$ to about $5\times10^8$ molecules of the active agent, such as $1\times10^5$ to about $5\times10^7$ molecules of the active agent, such as $1\times10^6$ to about $5\times10^6$ molecules of the active agent, and may include more, or less, of the active agent.

According to embodiments, a cargo to be delivered to the interior of a cell via the peptisomes is contacted with a fluorine-containing cargo solubilizing agent to aid in miscibility with the perfluorocarbon liquid core. The fluorine-containing cargo solubilizing agent may be, for example, a perfluoroalkyl, a polyfluoroalkyl, a perfluorinated alkyl acid, a polyfluorinated alkyl acid, a perfluorinated aromatic compound, a polyfluorinated aromatic compound, any of which may be further substituted or unsubstituted, or a mixture of any two or more thereof. The fluorine-containing cargo solubilizing agent may be, for example, perfluorooctane $(CF_3(CF_2)_6CF_3)$, perfluoroteradecane $(CF_3(CF_2)_{12}CF_3)$, trifluoroacetic acid $(CF_3COOH)$, pentafluoropropionic acid $(CF_3(CF_2)COOH)$, perfluoropentanoic acid $(CF_3(CF_2)_3COOH)$, perfluorononanoic acid $(CF_3(CF_2)_7COOH)$, perfluorotetradecanoic acid $(CF_3(CF_2)_{12}COOH)$, perfluorooctadecanoic acid $(CF_3(CF_2)_{16}COOH)$, perfluorocyclohexanecarboxylic acid $((CF_2)_5CFCOOH)$, pentafluorophenol (2,3,4,5,6-pentafluorophenol, $C_6F_5OH$), pentafluorobenzaldehyde (2,3,4,5,6-pentafluorobenzaldehyde, $C_6F_5CHO$), or Fmoc-pentafluorophenylalanine $((CF)_5CCH_2C(NH\text{-}Fmoc)COOH$, Fmoc-pentafluoro-L-phenylalanine and/or. Fmoc-pentafluoro-D-phenylalanine, or a mixture of any two or more thereof, but is pot limited thereto. In an embodiment, the fluorine-containing cargo solubilizing agent may be perfluorononanoic acid.

In another embodiment, a composition including the above peptisome is provided that may be used for therapeutic or diagnostic use. The composition may include a pharmaceutically acceptable excipient, for example, a vehicle, an adjuvant, a carrier or a diluent, that are well-known to those who are skilled in the art and are readily available to the public. Typically, the pharmaceutically acceptable carrier is one that is chemically inert to the pharmaceutically active agents and one that has no detrimental side effects or toxicity under the conditions of use.

The compositions may be administered as oral, sublingual, transdermal, subcutaneous, topical, absorption through epithelial or mucocutaneous linings, intravenous, intranasal, intraarterial, intramuscular, intratumoral, peritumoral, interperitoneal, intrathecal, rectal, vaginal, or aerosol formulations. In some aspects, the pharmaceutical composition is administered orally or intravenously. One preferred method of administration is through an intravenous injection.

In still another embodiment, a method of preparing the peptisome is disclosed. According to the method, a composition including a therapeutically active agent, an amphiphilic peptide represented by any of the above Formulas (I), (II), (III), (IV), or (V), and a perfluorocarbon liquid is provided. The composition is then contacted with water to provide an intermediate assembly including a perfluorocarbon liquid core containing the perfluorocarbon liquid and the therapeutically active agent dispersed in the perfluorocarbon liquid, and a plurality of amphiphilic peptides surrounding the perfluorocarbon liquid core. In the intermediate assembly, the amphiphilic peptides are oriented in such a way that the groups HB are interpolated into the perfluorocarbon liquid of the perfluorocarbon liquid core, while the groups HP extend away from the surface of the perfluorocarbon liquid core and away from the core of the perfluorocarbon liquid core. The amphiphilic peptide molecules of the intermediate assembly are subsequently cross-linked to form the peptisomes.

The water may have a temperature of 10° C. or lower, for example, 9° C. or lower, 8° C. or lower, 7° C. or lower, 6° C. or lower, 5° C. or lower, 4° C. or lower, 3° C. or lower, 2° C. or lower, or 10° C. or lower. In an embodiment, the water may be ice-cold water. While not wishing to be bound to any theory, it is understood that when cold water is slowly added to an organic emulsion of amphiphilic peptides and perfluorocarbon liquid, spontaneous assembly of the amphiphilic peptides at the surface of the perfluorocarbon liquid core takes place. This mild procedure also eliminates the need for aggressive synthetic methods commonly used to prepare stimuli-responsive particles, which can lead to degradation of the encapsulated therapeutically active agent.

According to embodiments of methods of making peptisomes, a cargo to be delivered to the interior of a cell via the peptisomes is contacted with a fluorine-containing cargo solubilizing agent to aid in miscibility with the perfluorocarbon liquid core. The fluorine-containing cargo solubilizing agent may be, for example, a perfluoroalkyl, a polyfluoroalkyl, a perfluorinated alkyl acid, a polyfluorinated alkyl acid, a perfluorinated aromatic compound, a polyfluorinated aromatic compound, any of which may be further substituted or unsubstituted, or a mixture of any two or more thereof. The fluorine-containing cargo solubilizing agent may be, for example, perfluorooctane ($CF_3(CF_2)_6CF_3$), perfluoroteradecane ($CF_3(CF_2)_{12}CF_3$), trifluoroacetic acid ($CF_3COOH$), pentafluoropropionic acid ($CF_3(CF_2)COOH$), perfluoropentanoic acid ($CF_3(CF_2)_3COOH$), perfluorononanoic acid ($CF_3(CF_2)_7COOH$), perfluorotetradecanoic acid ($CF_3(CF_2)_{12}COOH$), perfluorooctadecanoic acid ($CF_3(CF_2)_{16}COOH$), perfluorocyclohexanecarboxylic acid ($(CF_2)_5CFCOOH$), pentafluorophenol (2,3,4,5,6-pentafluorophenol, $C_6F_5OH$), pentafluorobenzaldehyde (2,3,4,5,6-pentafluorobenzaldehyde, $C_6F_5CHO$), or Fmoc-pentafluorophenylalanine (($CF)_5CCH_2C(NH-Fmoc)COOH$. Fmoc-pentafluoro-L-phenylalanine and/or Fmoc-pentafluoro-D-phenylalanine, or a mixture of any two or more thereof, but is not limited thereto. In an embodiment, the fluorine-containing cargo solubilizing agent may be perfluorononanoic acid.

According to embodiments of methods of making peptisomes, the fluorine-containing cargo solubilizing agent, the perfluorocarbon liquid, and the cargo are mixed together and the amphiphilic peptides represented by any of the above Formulas (I), (II), (III), (IV), or (V), are added, forming a composition. The composition is then contacted with water to provide an intermediate assembly including a perfluorocarbon liquid core containing the perfluorocarbon liquid and the therapeutically active agent dispersed in the perfluorocarbon liquid, and a plurality of amphiphilic peptides surrounding the perfluorocarbon liquid core. In the intermediate assembly, the amphiphilic peptides are oriented in such a way that the groups HB are interpolated into the perfluorocarbon liquid of the perfluorocarbon liquid core, while the groups HP extend away from the surface of the perfluorocarbon liquid core and away from the core of the perfluorocarbon liquid core. The amphiphilic peptide molecules of the intermediate assembly are subsequently cross-linked to form the nanopeptisomes.

According to embodiments, the peptisomes have an average diameter in the range from about 1 micron to about 5 microns. According to embodiments, the peptisomes are nanopeptisomes having an average diameter in the range from about 250 nanometers to about 1000 nanometers. According to embodiments, the peptisomes are nanopeptisomes having an average diameter in the range from about 250 nanometers to about 750 nanometers. The size of peptisomes can be controlled by varying the volume percent (vol %) of the perfluorocarbon liquid and/or the concentration of amphiphilic peptide in the composition when making the peptisomes, see for example FIG. 4 and FIG. 14. In general, the volume percent of the perfluorocarbon liquid can be increased to increase the average diameter of the peptisomes, but this increase in average diameter is limited if the concentration of amphiphilic peptide is not also increased. According to embodiments, the volume percent of the perfluorocarbon liquid can be increased to increase the average diameter of the peptisomes with a standard amount of amphiphilic peptides, along with simultaneous additional preparations in which the amount of amphiphilic peptides is varied to obtain a population of peptisomes with a desired average diameter.

During preparation, the cross-linking may be performed during a dialysis of the intermediate assembly. The dialysis may be conducted in an aqueous solution including dimethylsulfoxide or any other organic solvent capable of oxidizing and cross-linking thiol groups of cysteine amino acids. For example, the dialysis may be carried out in an aqueous solution of dimethylsulfoxide (DMSO) at any concentration. In an embodiment, the dialysis can be carried out in a 2.5% solution of DMSO in water. This mild cross-linking procedure also eliminates the need for aggressive synthetic methods commonly used to prepare stimuli-responsive particles, which can lead to degradation of the encapsulated cargo of the therapeutically active agent.

The degree of cross-linking of the amphiphilic peptide molecules is about 60% or greater, for example, about 65% or greater, about 70% or greater, about 75% or greater, about 80% or greater, about 85% or greater, about 90% or greater, or about 95% or greater. The degree of cross-linking of the amphiphilic peptides can be determined by a colorimetric disulfide formation assay.

In another embodiment, a method of delivering an active agent to a target cell is provided. According to the method, a composition including the above peptisome loaded with, for example a therapeutic or diagnostic active agent is prepared. The composition is then administered to a patient, and an ultrasound radiation is applied to release the therapeutically active entity from the peptisome.

In another still embodiment, a method of inhibiting growth of cancer cells is provided. The method includes the steps of contacting the cancer cells with a composition containing a peptisome of the present invention and applying ultrasound radiation to release the therapeutically active entity from the peptisome.

In yet another embodiment, a method of treating cancer in a patient is provided. The method includes the steps of administering a composition containing the above peptisome to the patient and applying ultrasound radiation to a diseased tissue of the patient to release the therapeutically active entity from the peptisome.

According to embodiments, peptisomes and nanopeptisomes are utilized in ultrasound imaging methods. Peptisomes having an average diameter of >1 micron provide good acoustic contrast and thus are useful as imaging agents. Such peptisomes are too large to leave blood vessels and therefore are particularly useful in vascular applications, such as targeted imaging for diagnosis and/or targeted treatment of atherosclerotic plaques or blood clots. For vascular applications of the micron-sized peptisomes, a targeting agent can be included in the hydrophilic amino acid sequence of the amphiphilic peptides and used to target atherosclerosis or blood clots such as CRKRLDRNC (SEQ ID NO:43) which binds to the IL-4 receptor on atherosclerotic plaques; EFEEFEIDEEEK (SEQ ID NO:44) which binds to thrombin in blood clots; and/or DFEEIPEEYLQ (SEQ ID NO:45) which binds to thrombin in blood clots. Such targeted peptisomes are injected systemically into blood vessels for diagnosis and/or targeted treatment.

In contrast, nanopeptisomes <750 nm in diameter can leave blood vessels in diseased tissues and other tissues and distribute to cells, thereby allowing for cargo delivery, including targeted cargo delivery, such as delivery of drugs and biologics including, but not limited to, small molecules, proteins and nucleic acids.

For imaging, two modalities of ultrasound imaging can be used. B-mode ultrasound imaging, allows viewing of stable peptisomes that have cores vaporized under low intensity ultrasound to form microbubbles—but have not yet collapsed or lysed. B-mode ultrasound imaging allows a user to view and guide the peptisomes in space using the ultrasound pressure wave. Doppler imaging can be used and allows viewing of changes in frequency that occur when the peptisomes collapse due to application of ultrasound. Thus, Doppler imaging can be used to confirm carrier lysis and cargo release using higher ultrasound energies.

The term "low intensity" is used to refer to ultrasound at acoustic pressures that allow the core of the peptisomes to oscillate as bubbles but not collapse. The term "high intensity" is used to refer to ultrasound at acoustic pressures that cause bubble cavitation of the peptisome cores. The exact threshold defining where low intensity stops, and high intensity starts will depend on the nature of the peptide shell and size of the peptisomes. In general, application of ultrasound to a patient is at an ultrasound intensity of no higher than 1.9 MI. For example, the 500 nm nanopeptisomes wherein the amphiphilic peptides have the sequence $F_FF_FF_F$GGGCCGGKGRGD-NH$_2$ (SEQ ID NO:49), stably oscillate as bubbles below 0.4 MI (mechanical index, measure of ultrasound intensity), and collapse at ultrasound pressures above this threshold.

In yet another embodiment, a method of treating bacterial infection in a patient is provided. The method includes the steps of administering a composition containing the peptisomes, such as nanopeptisomes, wherein the amphiphilic peptides of the peptisomes include a bacterial targeting agent, and wherein the cargo of the peptisomes is an antibacterial agent, to the patient and applying ultrasound radiation to a bacterially infected tissue of the patient to release the therapeutically active entity from the peptisome.

The present disclosure is illustrated and further described in more detail with reference to the following non-limiting examples.

EXAMPLES

Materials and General Methods

Fmoc-protected amino acids were purchased from Novabiochem. PL-Rink resin was purchased from Polymer Laboratories. 1H-Benzotriazolium 1-[bis(dimethylamino) methylene]-5chloro-hexafluorophosphate (1-),3-oxide (HCTU) was obtained from Peptides International. Trifluoroacetic acid was obtained from Acros organics, and 1,2-ethanedithiol was purchased from Fluka, Oregon Green 514 Phalloidin, 6 and 24 well cell culture plates, polystyrene microcuvettes, diethyl ether, dimethylformamide (DMF), acetonitrile (ACN), N-methylpyrrolidone (NMP), Slide-A-Lyzer™ dialysis cassettes (MWCO 3.5K) and 96-well half area high content imaging glass bottom microplates were purchased from Fisher Scientific. Perfluorohexane (PFH) and perfluoropentane (PFP) were purchased from Oakwood Chemicals and Strem Chemicals, respectively. N,N-diisoproylcarbodiimide (DIC) was purchased from Chem Impex. Thioanisole, anisole, 3-(4,5-dimethyl-2-thiazolyl)-2,5-diphenyl-2H-tetrazolium bromide (MTT), 2,2'-dithiodipyridine (DTP), dimethyl sulfoxide (DMSO), 1,8-diazabicyclo [5.4.0]undec-7-ene (DBU) and 200 mM glutamine solution were obtained from Sigma-Aldrich. RPMI-1640 media, Hanks Balanced Salt Solution (HBSS) and Hoechst 33342 trihydrochloride dye was purchased from Invitrogen. Phosphate buffered saline (PBS) IX without calcium and magnesium, and L-glutamine (L-Gln), were purchased from Corning. Heat inactivated fetal bovine serum (FBS) and trypsin EDTA were obtained from Hyclone Laboratory Inc. IHPLC solvents consisted of solvent A (0.1% TFA in water) and solvent B (0.1% TFA in ACN). Gentamycin was purchased from VWR. RPMI-1640 without L-glutamine was purchased from Lonza. Hoechst 33342 and UltraPure™ agarose were purchased from Invitrogen. 4% paraformaldehyde in PBS was purchased from Chem Cruz. The green fluorescent protein (GFP, 36 kDa) was obtained from Dr. J. P. Schneider (Chemical Biology Laboratory, NCI) and A549 human cancer cell line was obtained from the NCI-60 repository. All peptides utilized for experiments were prepared with an amidated C-terminus.

Peptide Synthesis

Fmoc-based solid-phase peptide chemistry was used to prepare the amphiphilic peptides, with HCTU activation on PL-Rink resin using an automated ABI 433A peptide synthesizer. Amphiphilic peptides were cleaved from the resin and simultaneously side-chain deprotected using a trifluoroacetic acid/thioanisole/1,2-ethanedithiol/anisole (90:5:3:2) cocktail for 2 hours under argon atmosphere. The crude product was precipitated with cold diethyl ether and then lyophilized. Amphiphilic peptides were purified via reverse-phase HPLC equipped with a FluoroFlash) semi-preparative column composed of silica gel bonded with perfluoroocty-lethylsilyl ($Si(CH_2)_2C_8F_{17}$). A gradient of 0-50% solvent B over 25 min., followed by 50-100% solvent B over an additional 50 min. was utilized. All amphiphilic peptides were lyophilized to collect the pure product, and the purity verified by analytical HPLC-MS.

Peptisome and Nanopeptisome Formation

Peptides were weighed out as a dry fluffy solid in a round bottom flask, and dissolved in a volume of 1:1 DMF:ACN containing 1% TFA to a final concentration of 0.5-2.0 mg/mL. The solution was stirred at 1,000 rpm on ice for 15 min. before addition of 1%-2% (v/v) cold PFP. After an additional 5 min. of stirring to properly mix the components and create an emulsion, an equal volume of cold MilliQ water was slowly added dropwise. During this solvent exchange procedure the solution turned opaque due to self-assembly of the peptides at the interface of the water-PFP emulsion. The mixture was stirred at 1,000 rpm for 1 hour on ice, over which time the solution clarified. Unincorporated peptide was removed by dialyzing the mixture against MilliQ water containing 2.5% (v/v) DMSO to oxidize the cysteines and facilitate disulfide cross-linking of the amphiphilic peptides of the nanopeptisomes. In addition, a Pasteur pipette was used to gently bubble air into the media to further promote oxidation, Dialysis was performed for 12 hours, with exchanges every four hours. Two final exchanges of the dialysis media to pure MilliQ water, for 2 hours each, removed residual DMSO. The purified nanopeptisomes were removed from the dialysis cassette, placed into a clean glass vial and used for experiments within 48 hours.

Physico-Chemical Characterization

Particle size and zeta potential measurements were performed via dynamic light scattering using a Zetasizer Nano-ZS instrument (Malvern, Worcestershire, UK). For size determination, a solution of nanopeptisomes in water was diluted times into characterization buffer (25 mM Tris-HCl, 150 mM NaCl, pH 7.4) to reach a final volume of 1 mL in a clean polystyrene microcuvette. The size of pure 1-2 vol % PFP emulsions prepared in 1:1 DMF:ACN containing 1% TFA were also measured as controls. Three independent measurements, ten runs each, were taken at a 1750 scattering angle, a sample position of 4.65 mm and an attenuation of 11. Particle size was recorded at both 25° C. and 37° C., with a 2 min. sample equilibration time. Material refractive index (RI) was set at 1.59 (25° C.) and 1.45 (37° C.) using pre-defined settings provided by the manufacturer. Dispersant RI of 1.332 and viscosity [cP] equal to 0.9103 (25° C.) and 0.7096 (37° C.) were calculated using the 'Solvent Builder' tool in the Zetasizer software. Phase analysis light scattering (PALS) assisted zeta potential measurements were performed by adding the solution of nanopeptisomes to MilliQ water to achieve a ten-fold dilution, and loading 700 µL of the sample into a disposable folded capillary cell (Malvern, DTS 1070). Three independent measurements were taken at 25° C., with twenty runs each.

In separate studies, the stability of nanopeptisomes during storage was evaluated via dynamic light scattering. Here, purified particles (formulation B of Table 2) were dispersed into milliQ water and left at room temperature. At defined time points over 15 days an aliquot was removed, diluted ten times into characterization buffer, and particle size and count rate recorded at 25° C. Of note, count rate was used as a qualitative indicator of particle density and thus an estimate of stability over time. In parallel experiments, the same particles were initially diluted ten times into blank characterization buffer, or buffer supplemented with 5% fetal bovine serum, and incubated at 37° C. to evaluate their stability under physiologic conditions. At defined time points over 48 hours a 1 mL aliquot was directly added to a clean polystyrene microcuvette and particle size measured at 37° C. For both experiments, three independent measurements were taken with twenty runs each.

Nanopeptisome Visualization

Differential interference contrast (DIC) microscopy was used to image the nanopeptisomes in solution. Briefly, nanopeptisomes were diluted two times into characterization buffer and added to 96-well glass bottom high-content imaging microplates. The plates were then loaded onto an LSM 710 confocal microscope (Zeiss, Thornwood, NY) equipped with a temperature controlled humidified chamber. Images were collected at 25° C. and 37° C., with a 15 min. sample equilibration time, using a 63× Plan-Apochromat oil objective.

Disulfide Formation Assay

A 1.5 mL solution of freshly prepared nanopeptisomes in water (0.5 mg/mL peptide and 2% PFP) was placed in a round bottom flask and slowly stirred with gentle bubbling of air. A 2.5% volume of DMSO was added to oxidize the thiols and initiate cross-linking. At specific time points, a 30 µL aliquot of the mixture was diluted into 200 µL of 0.1 mM DTP in characterization buffer, and allowed to react for 10 min. The solution was then transferred to a quartz cuvette (1 cm pathlength) and concentration of the free thiolate was determined via absorption at 343 nm ($\varepsilon_{343}$=7600 cm$^{-1}$M$^{-1}$) (Haines et al., 2005) using an Agilent 8453 UV-Vis spectrophotometer (Santa Clara, CA). In separate control experiments, the same procedure was followed without the addition of 2.5% (v/v) of DMSO to evaluate its influence on thiol oxidation and disulfide cross-linking of nanopeptisomes. All values were corrected for background DTP hydrolysis. Percentage of disulfide formation was calculated by subtracting the concentration of free thiolate from the initial cysteine concentration. Studies were performed in triplicate.

Phalloidin Loading and Ultrasound Delivery

Nanopeptisomes were prepared at 0.5 mg/mL peptide and 2% PFP containing fluorescently-labeled Phalloidin and used for in vitro experiments within 24 hours of their preparation. Briefly, 500 µL of cold PFP was added to 300 U of Oregon Green 514 Phalloidin and stirred vigorously on ice for 3 hours. An aliquot of the PFP-Phalloidin mixture was then added to the peptide solution, and nanopeptisomes formed and purified as described above. To evaluate encapsulation efficiency, a 100 µL aliquot of phalloidin-loaded peptisomes in water was added to a clean quartz microcuvette and UV spectra collected from 200-1000 nm. Absorbance maxima of Oregon green 514 at 506 nm allowed for the calculation of phalloidin concentration using the manufacturer reported extinction coefficient for the fluorescent label (ThermoFisher Scientific, $\varepsilon$=85,000 M$^{-1}$ cm$^{-1}$). To calculate per particle loading of phalloidin, nanopeptisome concentration (formulation B of Table 2) was measured in water using a Malvern NanoSight LM 10 with a camera level of 9, slider shutter of 607, slider gain of 15 and 25 FPS.

Analysis settings included a detect threshold of 5 and auto blur size. For these experiments, unloaded particles were measured to avoid interference of the fluorescently-labeled cargo with the NanoSight particle tracking software.

For flow cytometry studies, A549 cells were suspended in HBSS and added to 24 well plates at $2 \times 10^5$ cells/well. Phalloidin-loaded nanopeptisomes, diluted in HBSS, were added to the cell suspension to achieve a final density of $2.24 \times 10^7$ particles/mL in a total volume of 500 µL. Plates were rocked in the dark at 70 rpm and 37° C. for four hours to allow for cellular binding of the perfluorocarbon liquid cores. This incubation period was selected based on previous work indicating a 4 hour incubation of cancer cells with RGD-labeled nanoparticles is sufficient to afford integrin-mediated cell surface binding (Majumder et al., 2014). After this time, the cells were washed with warm HBSS to remove unbound nanopeptisomes and 500 µL of fresh HBSS added. As a control, a volume of Phalloidin-PFP, similar to that used in formulation of Phalloidin-loaded nanopeptisomes, was diluted in HBSS at a total volume of 500 µL and added to separate plates containing A549 cells. Insonation of the samples was performed using a Vevo® Sonigene™ low frequency ultrasound device (Visualsonics, Toronto, ON, Canada), equipped with a 1 MHz, 10 mm diameter transducer with an unfocused beam. The transducer was fixed to a ring stand, and lowered until it touched the surface of the sample solution (~0.5 cm from the bottom of the plate). Ultrasound was applied for 90 sec at a duty cycle of 10%-20% with intensity varied between 0.1-1.0 W/cm$^2$, corresponding to a peak negative pressure of 0.054-0.172 mPa, respectively. Samples were then placed in the incubator for 15 min. before addition of 500 µL of fresh HBSS. Cells were then collected and placed on ice, before analysis using a Beckman Coulter FACsCalibur flow cytometer (488 nm excitation laser). Gating was based on normalized fluorescence of untreated cells to evaluate the fluorescence increase of cells treated under the different conditions. Studies were performed in triplicate for each experimental condition.

In separate experiments, A549 cells were seeded onto 6 well plates at $5 \times 10^5$ cells/well and allowed to adhere overnight. Cells were washed with fresh HBSS, followed by addition of 3 mL of HBSS containing Phalloidin-loaded nanopeptisomes at a concentration of $2.24 \times 10^7$ particles/mL. After a four hour incubation period the cells were washed with HBSS and 3 mL of fresh buffer added to each well. Ultrasound was applied at 0.5 W/cm$^2$, 20% duty cycle for 90 sec. to each well, and plates incubated for 15 min. During this time 2 µg/mL Hoechst 33342 dye was added to the solution to stain cell nuclei. To evaluate co-localization of delivered phalloidin and endosomes, a 30 &L, aliquot of 5 mg/mL Texas Red-Transferrin (ThermoFisher Scientific) in milliQ water was added to treated cells to achieve a final concentration of 50 µg/mL, and plates incubated for 30 min. Following removal of the supernatant, washing with warm HBSS and addition of 3 mL fresh buffer, plates were mounted onto an EVOS FL Auto fluorescent microscope (Life Technologies, Grand Island, NY) equipped with an environmental chamber to maintain 37° C. and 5% COZ during experiments. Cells were imaged at 10× or 20× magnification using the manufacturer LED light cubes for DAPI (357/44 nm excitation, 447/60 nm emission), GFP (470/22 nm excitation, 510/42 nm emission) and Texas Red (585/29 nm excitation, 628/32 nm emission).

Cell Viability Assay

A549 cells were seeded onto 6 well plates at $5 \times 10^5$ cells/well and allowed to adhere overnight. Cells were then washed and 3 mL of warm HBSS added to each well. Ultrasound was applied for 90 sec at a duty cycle of 10%-20% with intensity varied between 0.1-1.0 W/cm$^2$, corresponding to a peak negative pressure of 0.054-0.172 mPa, respectively. Wells not subjected to US, or cells incubated with 25% DMSO in HBSS for 1 hour, were used as negative and positive controls, respectively. Following US insonation, cells were incubated for 30 min. to recover and then washed with warm HBSS. 3 mL of a 0.5 mg/mL solution of MTT reagent in HBSS was added to each well and incubated for 2 hours. The supernatant was removed and replaced with 3 mL of DMSO to dissolve the formazan product, followed by transfer of a 100 µL aliquot of the colored solution to a 96 well plate. Absorbance was then read at 540 nm using a UV plate reader (Biotek, Winooski, VT). The absorbance of negative controls was subtracted from each sample as a blank, and percent viability calculated using the equation: (Absorbance$_{US\text{-}treated\ cells}$/Absorbance$_{untreated\ cells}$)×100. Results shown represent the average of three independent experiments±standard deviation.

Results

As evidenced by the above data, the denovo designed peptide F$_F$F$_F$F$_F$GGGCCGGKGRGD-NH$_2$ (SEQ ID NO:49) is capable of assembling at the surface of a perfluoro-n-pentane (PFP) droplet. The peptide sequence contains three pentafluoro-phenylalanine (F$_F$) residues at its N-terminus, which promotes interpolation and assembly of the peptide at the PFP-liquid interface. C-terminal to this fluorous domain is a cysteine containing motif, GGGCCGG (SEQ ID NO:46), designed to undergo disulfide cross-linking to stabilize the peptide corona after templated assembly. Incorporation of a bioactive hydrophilic sequence at the peptide's C-terminus ultimately leads to its multivalent display at the surface of the assembled particle. In this particular design, the sequence KGRGD (SEQ ID NO:35) has been included to enable cell-surface localization of the nanoparticle mediated by binding of RGD with extracellular integrins. Despite inclusion of highly fluorinated residues, this sequence was able to be chemically synthesized in high yield and purity using standard solid-phase techniques.

Figure 3:
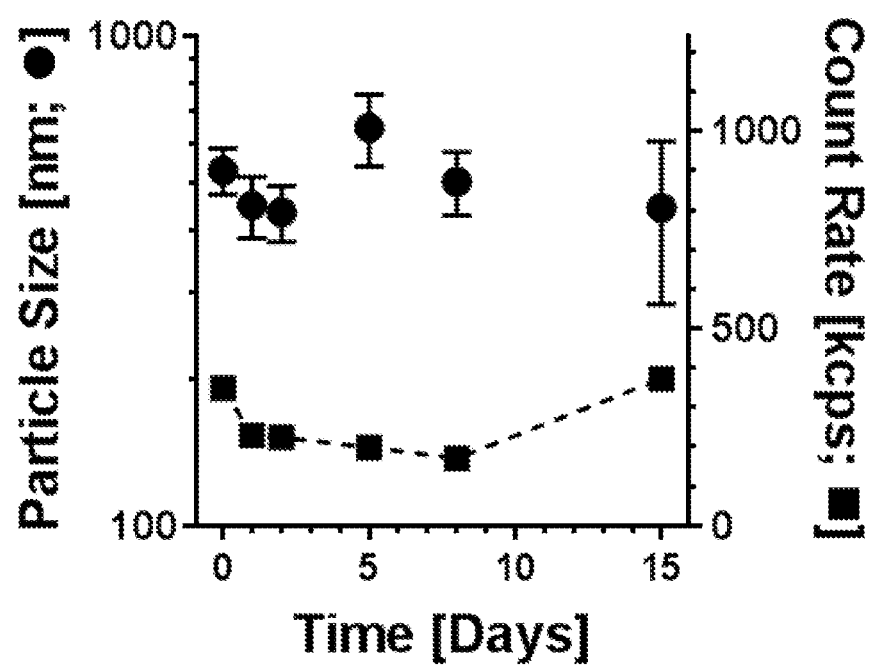
FIG. 3 is a graph of particle size (nanometers, nm) and count rate (kilo counts per second, kcps) versus time (days) illustrating stability of nanopeptisomes (formulation B, see Table 2) during long-term storage in water at room temperature, wherein particle stability was measured via DLS over 15 days.

It has been found that, to form peptisomes and nanopeptisomes, a solvent-exchange procedure in which cold water is slowly added to an organic emulsion of amphiphilic peptides and PFP, ultimately leads to spontaneous assembly of the amphiphilic peptides at the surface of PFP liquid core. Importantly, this mild procedure eliminates the need for aggressive synthetic methods commonly used to prepare stimuli-responsive particles, which can lead to degradation of the encapsulated cargo. Subsequent dialysis against 2.5% DMSO in water removes unincorporated peptide, and promotes disulfide cross-linking of cysteine residues in the perfluorocarbon liquid core corona. Cross-linked nanopeptisomes remain stable for multiple weeks when stored at room temperature in water (FIG. 3).

Figure 14:
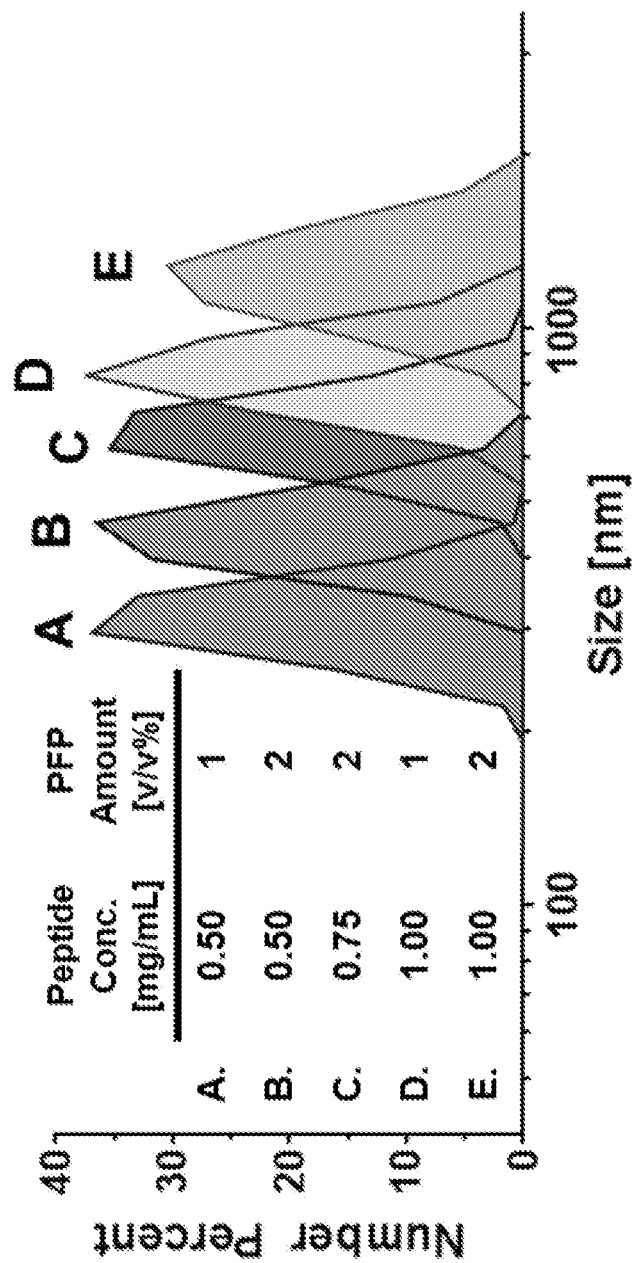
FIG. 14 is a graph of number percent versus particle size (nanometers, nm) illustrating particle size measurement of nanopeptisomes formulated under various peptide and PFP ratios, where each letter, A, B, C, D, and E, corresponds to different formulations shown in Table 2.

It has also been found that the size of nanopeptisomes could be precisely controlled between 250 nm and 1,200 nm, as a function of peptide and PFP feed ratio (FIG. 14, Table 2).

TABLE 2

Physicochemical properties of nanopeptisome formulations

| Formulation | Amphiphilic Peptide Conc. [mg/mL] | PFP [vol %] | Droplet size [nm] 25° C. | Droplet size [nm] 37° C. | Δ [b] | ζ [c] [mV] |
|---|---|---|---|---|---|---|
| E | 1.00 | 2 | $1.2 \times 10^3$ | $43 \times 10^3$ | 36.5 | 3.5 ± 0.2 |
| D | 1.00 | 1 | 863 ± 98 | $23 \times 10^3$ | 26.7 | 0.1 ± 0.2 |
| C | 0.75 | 2 | 739 ± 56 | $7.5 \times 10^3$ | 10.1 | 6.8 ± 0.5 |
| B*[a] | 0.75 | 1 | 469 ± 24 | 482 ± 34 | 1.0 | 8.0 ± 0.4 |
| B | 0.50 | 2 | 453 ± 29 | 528 ± 24 | 1.3 | 8.2 ± 0.4 |
| A*[a] | 0.25 | 2 | 448 ± 27 | 458 ± 23 | 1.0 | 4.6 ± 0.2 |
| A | 0.50 | 1 | 301 ± 14 | 390 ± 12 | 1.3 | 12.4 ± 0.4 |

[a] Formulations A* and B* are not shown in FIG. 14 due to their similar size formulation B.
[b] fold change in particle size at 37° C. versus 25 ° C.
[c] zeta potential.

Figure 4:
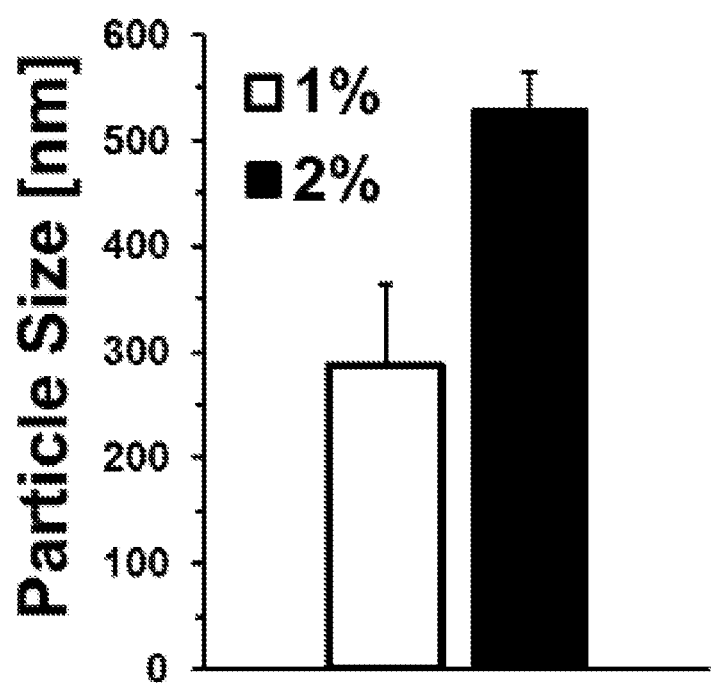
FIG. 4 is a diagram showing particle size of 1 and 2 vol % perfluoro-n-pentane (PFP) immediately after emulsion formation in the nanopeptisome pre-assembly solution (1:1 DMF:ACN, 1% TFA)

Dynamic light scattering performed on pure PFP emulsions indicates this may be due, in part, to different sizes of PFP droplets formed in the starting emulsion (FIG. 4). At any rate, the ability to control the hydrodynamic radii of the particles is critically important for delivery applications, as this parameter is inversely correlated with passive tissue distribution, and directly proportional to the US magnitude required for droplet cavitation.

Also evaluated was the influence of temperature on nanopeptisome size through direct visualization of particles in solution using differential interference contrast (DIC) confocal microscopy, as well as dynamic light scattering analysis. Results show that nanopeptisomes with a diameter <750 nm at 258° C. were able to maintain their size when heated to physiologic temperature, a vital requirement for acoustic droplet vaporization in vitro and in vivo (Shpak et al., 2014). Exceeding this size threshold led to premature PFP vaporization (bp=29 8° C.) and converted the perfluorocarbon liquid cores into gaseous microbubbles at 37° C., as evident by the massive increase in diameter for the purple, green and orange formulations. This influence of particle size on the vaporization temperature of PFP is due to the inverse relationship between internal pressure and droplet dimension, as described by the Laplace pressure Equation (1):

$$P_{in} = \frac{2\sigma}{R_H} + P_{atm} \tag{1}$$

where $P_{in}$ and $P_{atm}$ are the internal droplet pressure and atmospheric pressure, respectively, a is the interfacial surface tension and $R_H$ represents the hydrodynamic droplet radii. Here, decreasing the droplet size leads to an increase in the pressure exerted on the PFP core, ultimately keeping the fluorous liquid in a superheated state well above its bulk boiling point of 29° C. The influence of vapor pressure on the temperature of the PFP solvent can be defined using the Antoine vapor Equation (2):

$$T = \frac{B}{A - \log_{10} P} - C. \tag{2}$$

in which T and P represent temperature and pressure, respectively, while A, B, and C are equation parameters empirically determined for PFP (Barber et al., 1956). Combining the Laplace pressure (1) and Antoine vapor (2) equations provides a single expression describing the temperature at which the vapor pressure of the core is equal to the internal droplet pressure ($T_{vap}$), ultimately causing thermal droplet vaporization (3):

$$T_{vap} = \frac{B}{A - \log_{10}\left(\frac{2\sigma}{R_H} + P_{atm}\right)} - C \tag{3}$$

Figure 5:
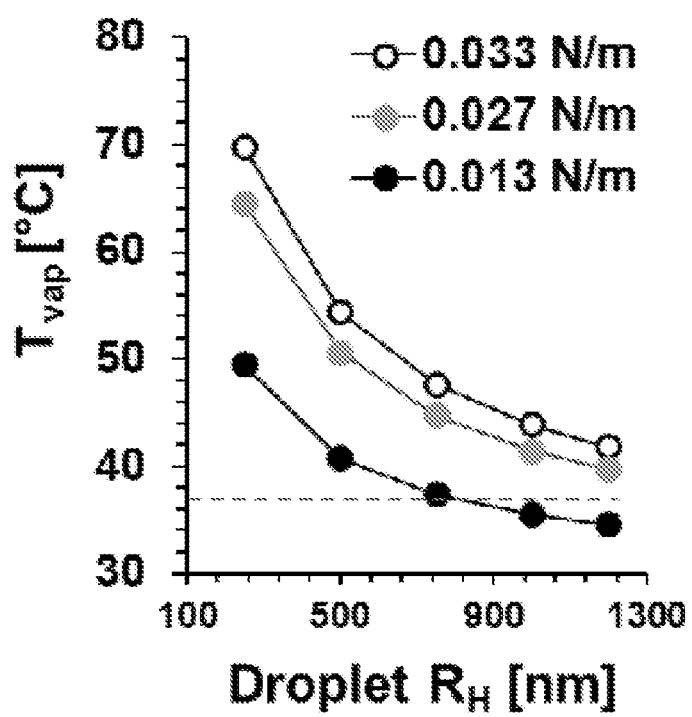
FIG. 5 is a graph showing relationship between PFP vaporization temperature ($T_{vap}$, degrees Centigrade, ° C.) and nanodroplet size ($R_H$, hydrodynamic radius, nanometers, nm), modeled at three different reported surface tension values for PFP emulsions formulated with the BSA protein (open circles), PEO-PLA polymer (filled gray circles) or CTAB surfactant (filled black circles), where the dashed line indicates physiologic temperature (37° C.)

Using this equation, the relationship between $T_{vap}$ and droplet size can be modeled using reported surface tension values for PFP emulsions formulated with either BSA (0.033 $Nm^{-1}$), the amphiphilic polymer PEO-PLA (0.027 $Nm^{-1}$), or the cationic surfactant cetrimonium bromide (CTAB; 0.013 $Nm^{-1}$) (FIG. 5) (Kandadai et al., 2010). Of note, the PFP-CTAB formulation most closely resembles the peptisomes reported here, in which the cationic amphiphilic sequence acts as the surfactant. Results from the model show that, at a surface tension of 0.013 $Nm^{-1}$, the vaporization point of the PFP core is expected to be >378° C. when particles are <800 nm in size, a finding that closely matches the experimental threshold identified for the PFP-peptide emulsions.

This suggests that the US energy required to thermally vaporize the nanopeptisome core could be carefully controlled by modulating the droplet size, as well as changing the interfacial surface tension through tuning the amphiphilic character of the assembling peptide.

Figure 6:
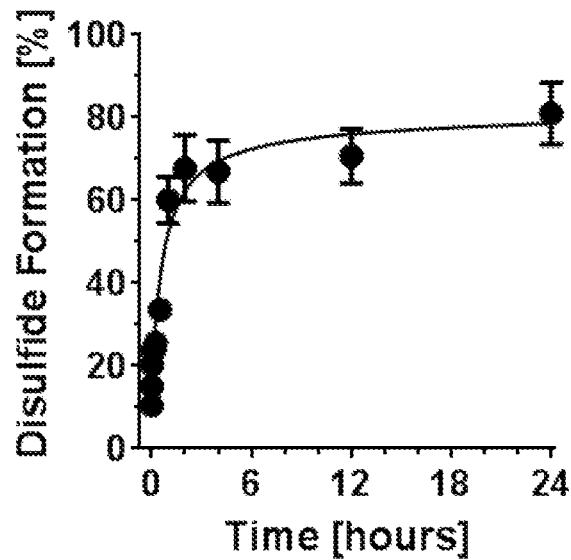
FIG. 6 is a graph showing peptisome cross-linking in the presence of 5% DMSO oxidizing agent used during dialysis purification.
Figure 7:
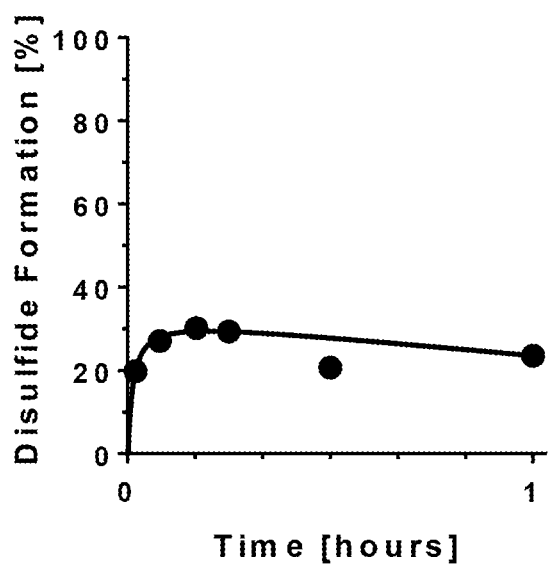
FIG. 7 is a graph of disulfide formation (percent, %) versus time (hours) illustrating percentage of disulfide cross-linking as a function of time following nanopeptisome assembly in formulation B (see Table 2) in the absence of DMSO, and showing that these nanopeptisomes were not stable beyond 1 hour.

Next, a series of experiments to test the stability of peptisomes in physiologic environments was performed, and their US-mediated delivery potential was evaluated. For these studies formulation B (FIG. 14, Table 2) was selected, as it remains a droplet at 37° C., and is predicted to have a core $T_{vap}$ slightly higher than physiologic temperature (~40° C.). This should, in theory, permit low intensities of US to be used to impart the additional thermal energy necessary for particle vaporization, thereby minimizing potential physical damage to cells and cargo during insonation. The stability of peptisomes was first evaluated by subjecting a buffered solution of the perfluorocarbon liquid cores to repeated thermocycling, during which dynamic light scattering was used to monitor particle integrity. Results show that peptisomes not only remained intact under these conditions, but showed little change in overall droplet size. Conversely, formulation E (FIG. 14, Table 2) spontaneously vaporized at 37° C. to form gaseous microbubbles, which then condensed back to their original size when cooled to room temperature. The stability of formulation B is likely imparted through the disulfide cross-links that are formed between cysteines of adjacent peptides in the peptisome corona. To investigate this possibility, the propensity of the cysteine resides to undergo oxidation by measuring the rate of disulfide bond formation within freshly prepared peptisomes was assessed (FIG. 6). Results from three independent samples showed that approximately 60% of the available thiols were cross-linked after 1 hour, with a maximum disulfide content of 80% achieved after 24 hours. Control experiments on freshly prepared peptisomes suspended in pure water, without the DMSO oxidizing agent, showed poor cross-linking (~20%) and loss of particle integrity 1 hour after their assembly (FIG. 7).

Figure 8:
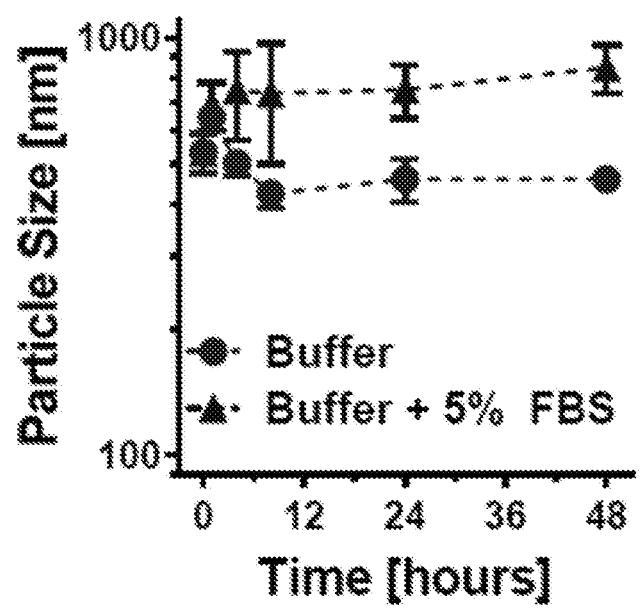
FIG. 8 is a graph of particle size (nanometers, nm) versus time (hours) illustrating stability of nanopeptisomes (formulation B, see Table 2) suspended in blank characterization buffer (25 mM, 150 mM NaCl, pH 7.4), or the same buffer supplemented with 5% fetal bovine serum, and incubated at 37° C. for 48 hours.

To assess the delivery potential of peptisomes fluorescently-labeled phalloidin, a cell-impermeable cyclic peptide that binds to intracellular filamentous actin, was loaded into the fluorous core of the particle and monitored its US-mediated transport into cells. Here, encapsulation of this model biomacromolecule was achieved simply by suspending it in the PFP solvent employed for templated assembly of the nanopeptisome carrier. UV spectroscopy performed on peptisomes containing the fluorescently-labeled cargo indicated an encapsulation efficiency of 81%, and an overall loading of $2.3 \times 10^6$ phalloidin per particle. Particles incubated with 5% FBS showed a small increase in size to approximately 700 nm, most likely due to physical adsorption of serum proteins to the cationic particle surface. Particle count rates were 150-200 kcps for both conditions during the incubation period, suggesting peptisomes remained stable in physiologic milieu. Particle sizing performed on peptisomes also confirmed the carrier remains stable under the physiologic conditions employed for delivery studies (FIG. 8).

Figure 9:
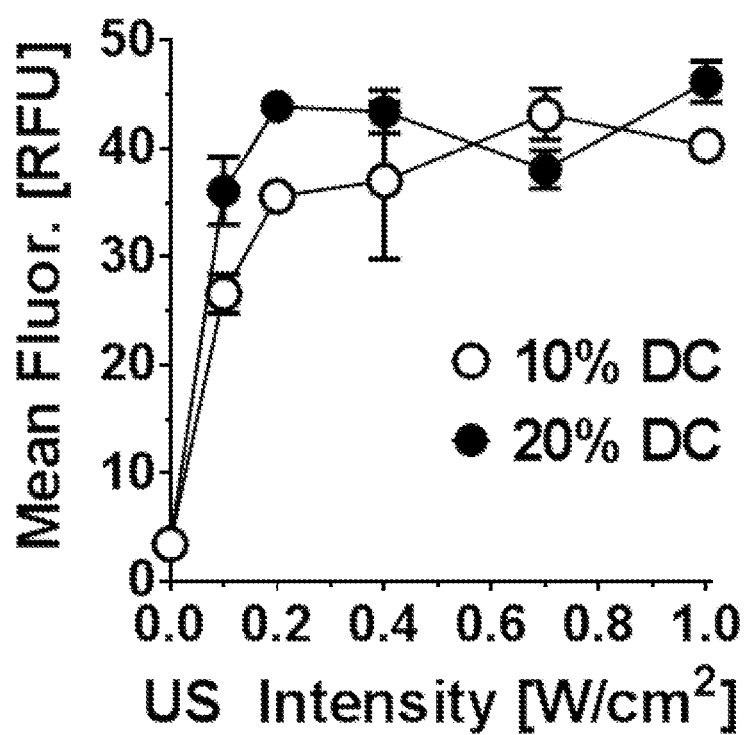
FIG. 9 is a graph showing mean intracellular fluorescence (relative fluorescence units, RFU) of A549 cells following delivery of labeled phalloidin from nanopeptisomes at varying ultrasound (US) intensity (watts per square centimeter, W/cm$^2$) and duty cycle (DC)
Figure 10:
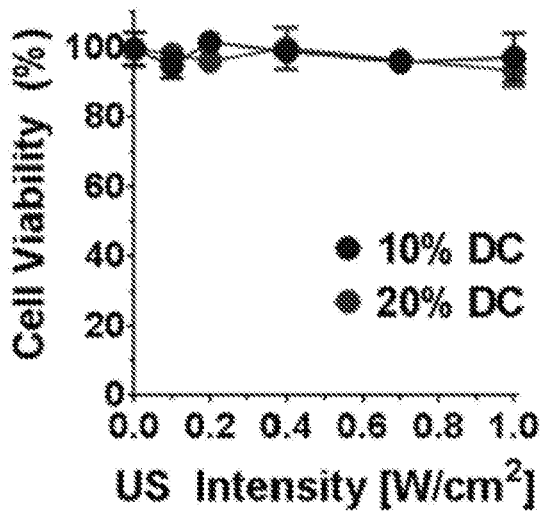
FIG. 10 is a graph of cell viability (percent, %) versus US intensity (watts per square centimeter, W/cm$^2$) illustrating viability of A549 cells subjected to insonation at 0.0-1.0 W/cm$^2$ intensities, using either a 10% or 20% US duty cycle (DC)

Using flow cytometry, the intracellular fluorescence of A549 lung carcinoma cells was measured following US-mediated phalloidin delivery from peptisomes, varying both the intensity of the acoustic signal and the pulse ratio (duty cycle; DC). Results in FIG. 9 show that, in the absence of the US trigger, peptisomes did not effectively deliver the encapsulated fluorescent cargo into cells (see data at 0.0 US intensity for both 10% and 20% DC, where intracellular fluorescence is near zero). However, at US intensities>0 W/cm$^2$ intracellular delivery of phalloidin increased as a function of increasing intensity for both DCs tested. Importantly, cells treated under these conditions of US remained viable and proliferative (FIG. 10). As a control, cells were subjected to insonation in the presence of unencapsulated phalloidin and PFP, to test the possibility that mechanical permeabilization of cells by US may be responsible for uptake of the fluorescently-labeled biomacromolecule.

Figure 11:
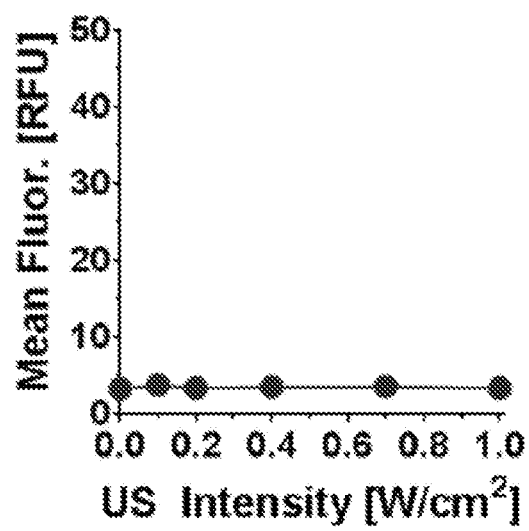
FIG. 11 is a graph of mean fluorescence (relative fluorescence units, RFU) of A549 cells treated with Oregon Green 514-labeled phalloidin dispersed in PFP, as a function of applied ultrasound intensity (20% duty cycle)

However, under these conditions no significant increase in intracellular fluorescence was observed across all tested US intensities (FIG. 11).

Figure 12:
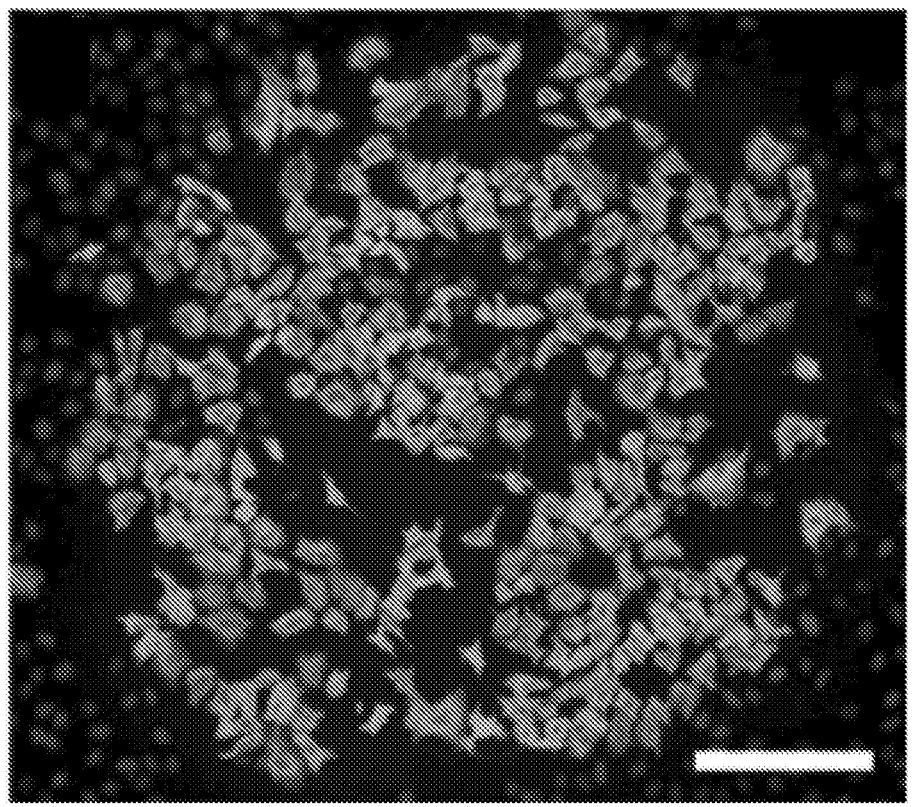
FIG. 12 is a live-cell image showing delivery of phalloidin (fluorescence is shown as bright cells) from nanopeptisomes into cells, spatially resolved to a circular area of the A549 cell monolayer subjected to US; cell nuclei are also stained and nuclei are visible in the periphery of the image without cytoplasmic fluorescence of phalloidin, the scale bar corresponds to 200 micrometers (μm)

Fluorescent microscopy performed on live cells after US-mediated delivery of labeled phalloidin confirmed that the cargo was transported into the cytoplasm and remained bioactive, as indicated by its ability to bind to intracellular actin filaments (FIG. 12; phalloidin visualized as green fluorescence). Importantly, phalloidin was only delivered to the circular area of the cell monolayer exposed to US, showing high spatial resolution over cargo release. The cells outside of the US insonated area showed no intracellular green fluorescence. Further, co-staining treated cells with fluorescently-labeled transferrin, an endosomal marker, showed limited co-localization with phalloidin fluorescence.

Figure 13:
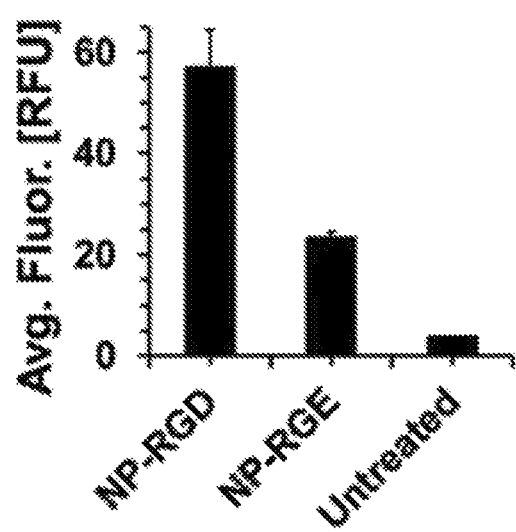
FIG. 13 is a diagram showing average intracellular fluorescence (relative fluorescence units, RFU) of A549 cells upon delivery of labeled phalloidin from nanopeptisomes (NP) wherein the amphiphilic peptides of the nanopeptisomes contained the RGD (NP-RGD) targeting motif compared to nanopeptisomes wherein the amphiphilic peptides contained the non-targeted control sequence RGE (NP-RGE)
Figure 15:
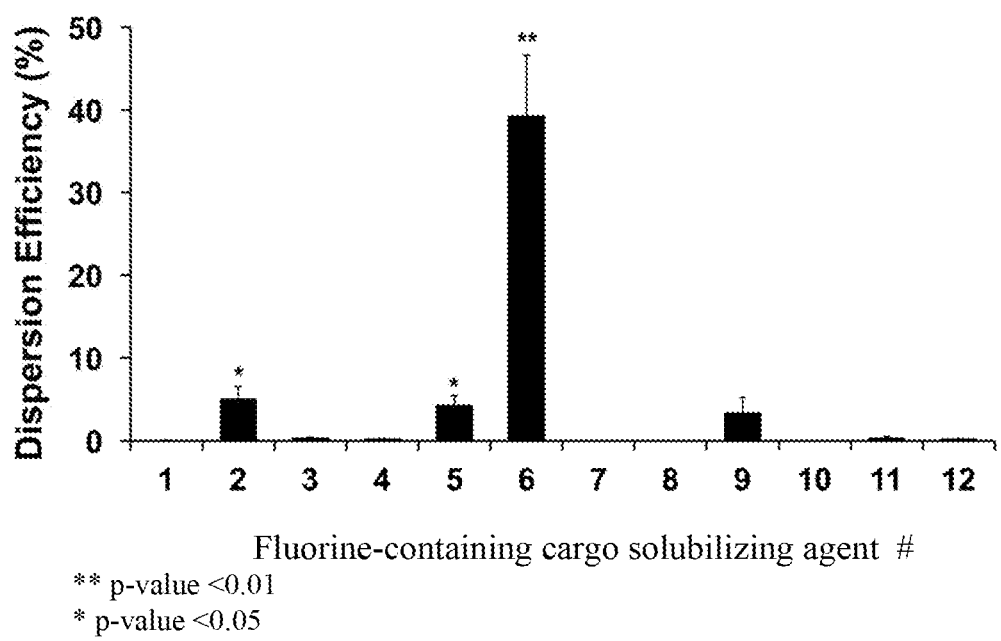
FIG. 15 is a graph that shows the results of screening of chemical fluorine-containing cargo solubilizing agents to identify candidates that promote protein loading into the fluorinated solvent core of peptisomes and nanopeptisomes.

This suggests that biomacromolecules delivered from peptisomes are directly shuttled to the cell cytoplasm and thereby avoid endosomal sequestration. Finally, cell-surface targeting of nanopeptisomes was evaluated by comparing the intracellular fluorescence of cells treated with RGD-containing peptisomes, loaded with labeled phalloidin, versus similar formulations prepared with the non-targeting control sequence RGE (FIG. 13). Results show that RGD-targeted carriers delivered roughly three times the amount of fluorescently-labeled phalloidin into cells compared to the RGE control. Although a moderate increase in cellular fluorescence was observed between untreated cells and those incubated with the non-targeted RGE particles, this is most likely due to non-specific electrostatic interactions between the cationic particle corona and the anionic cellular membrane. Collectively, these studies support an assertion that US-mediated rupture of peptisomes at the plasma membrane can directly deliver encapsulated bioactive macromolecules into the cytoplasm of cells.

As described herein, a new class of peptide-based nanodroplets, nanopeptisomes, capable of ultrasound-mediated delivery of membrane-impermeable cargo into cells has been developed. In this example, nanopeptisomes are prepared via the de novo designed peptide $F_FF_FF_FF_F$GGGCCGGKGRGD-$NH_2$ (SEQ ID NO:49), which efficiently assembles at the surface of organofluorine droplets, and undergoes cysteine-mediated cross-linking to stabilize the final nanostructure. Biomolecular cargo can be readily encapsulated within the nanopeptisome carrier during the assembly process. Cell binding of the nanopeptisomes, followed by acoustic vaporization, ultimately delivers the cargo into cells. Gaseous microbubbles generated during vaporization of peptisomes may also function as an US contrast agent to allow for imaging and guidance of the delivery modality in real-time. Thus, peptisomes of the present invention represent a potential theranostic system with broad applications in drug delivery and biomedical imaging.

Screening of Chemical Fluorine-Containing Cargo Solubilizing Agents

Twelve compounds were used in the screening to identify compounds that promote protein loading into the fluorinated solvent core of peptisomes and nanopeptisomes. The twelve candidate fluorinated compounds were identified and screened to promote protein dispersion within perfluorocarbons using the green fluorescent protein (GFP) as a model protein providing a fluorescent output to detect protein dispersion. Each candidate fluorinated compound was chosen based on fluorination degree and surfactant-like characteristics.

Twelve commercially available fluorine-containing cargo solubilizing agents: fluorine-containing cargo solubilizing agent #1 perfluorooctane ($CF_3(CF_2)_8CF_3$), fluorine-containing cargo solubilizing agent #2 perfluoroteradecane ($CF_3(CF_2)_{12}CF_3$), fluorine-containing cargo solubilizing agent #3 trifluoroacetic acid ($CF_3COOH$), fluorine-containing cargo solubilizing agent #4 pentafluoropropionic acid ($CF_3(CF_2)COOH$), fluorine-containing cargo solubilizing agent #5 perfluoropentanoic acid ($CF_3(CF_2)_3COOH$), fluorine-containing cargo solubilizing agent #6 perfluorononanoic acid ($CF_3(CF_2)_7COOH$), fluorine-containing cargo solubilizing agent #7 perfluorotetradecanoic acid ($CF_3(CF_2)_{12}COOH$), fluorine-containing cargo solubilizing agent #8 perfluorooctadecanoic acid ($CF_3(CF_2)_{16}COOH$), fluorine-containing cargo solubilizing agent #9 perfluorocyclohexanecarboxylic acid ($(CF_2)_5CHCOOH$), fluorine-containing cargo solubilizing agent #10 pentafluorophenol ($(CF_2)_5CHOH$), fluorine-containing cargo solubilizing agent #11 pentafluorobenzaldehyde (($CF_2$)$_5$CHCOH), and fluorine-containing cargo solubilizing agent #12 Fmoc-pentafluorophenylalanine (($CF_2$)$_5$CHCH$_2$NHCOOH-Fmoc), were each separately vortexed and sonicated to dissolve into perfluorohexane (PFH) at 0.01, 0.1, and 1 mM. For each condition, 200 ul of compounds+PFH was aliquoted into an Eppendorf tube containing individually dried GFP stocks (1 uM) for 9 replicates. Each tube was parafilmed, vortexed, placed on VWR tube rotator overnight at 4° C., and then centrifuged for 5 min at 4000 rpm. Next, 100 ul of each sample was aliquoted onto a black bottom 96-well plate for fluorescence scan from 500 to 560. The 96-well plate was then placed in 37° C. overnight to dry the PFH. The dry samples were resuspended in 100 ul PBS and scanned for fluorescence using BioTek Cytation 3 imaging reader. Results were compared to controls to determine % GFP fluorescence. Fluorinated compounds 2, 5, and 6 showed significant dispersion of GFP with 5.1%, 4.3%, and 39.3% efficiency, respectively, when compared to no fluorinated compound assistance after resuspension in aqueous buffer (FIG. 15). Compounds 3-8 are linear amphiphilic fluorinated carboxylic acids. Protein dispersion efficiency increases when the perfluorinated carbon chain length increases from 2 to 9. Conversely, increasing the chain length further prevents any protein dispersion. Compound 6, perfluorononanoic acid (PFNA), dispersed approximately 10-fold more protein within PFH compared to compound 5. The data shown in FIG. 15 indicates that fluorine-containing cargo solubilizing agent 6 (perfluorononanoic acid) was optimal among the compounds tested for solvation of GFP into the fluorinated solvent (PFH). Here, PFH is used as a surrogate for the penultimate solvent perfluoro-n-pentane (PFP) used to form the peptisome core, as PFP has a low boiling point and low surface tension, making it difficult to use in these screening experiments.

Fluorine-containing cargo solubilizing agent #6 (perfluorononanoic acid, PNFA) was dissolved at various concentrations in PFH to achieve molar ratios with GFP at 400:1 to 50,000:1 fluorine-containing cargo solubilizing agent-to-GFP. For this molar ratio screening, PFNA was vortexed and sonicated to dissolve into PFH at 0.4, 2, 50, and 100 mM. For each condition, 200 ul of PFNA+PFH was aliquoted into an Eppendorf tube containing individually dried GFP (1 uM) for 9 replicates. Each tube was parafilmed, vortexed, placed on VWR tube rotator overnight at 4° C., and then centrifuged for 5 min at 4000 rpm. Next, 100 ul of each sample was aliquoted onto a black bottom 96-well plate for fluorescence scan from 500 to 560. The 96-well plate was then placed in 37° C. overnight to dry the PFH. The dry samples were resuspended in 100 ul PBS and scanned for fluorescence using BioTek Cytation 3 imaging reader.

Figure 16:
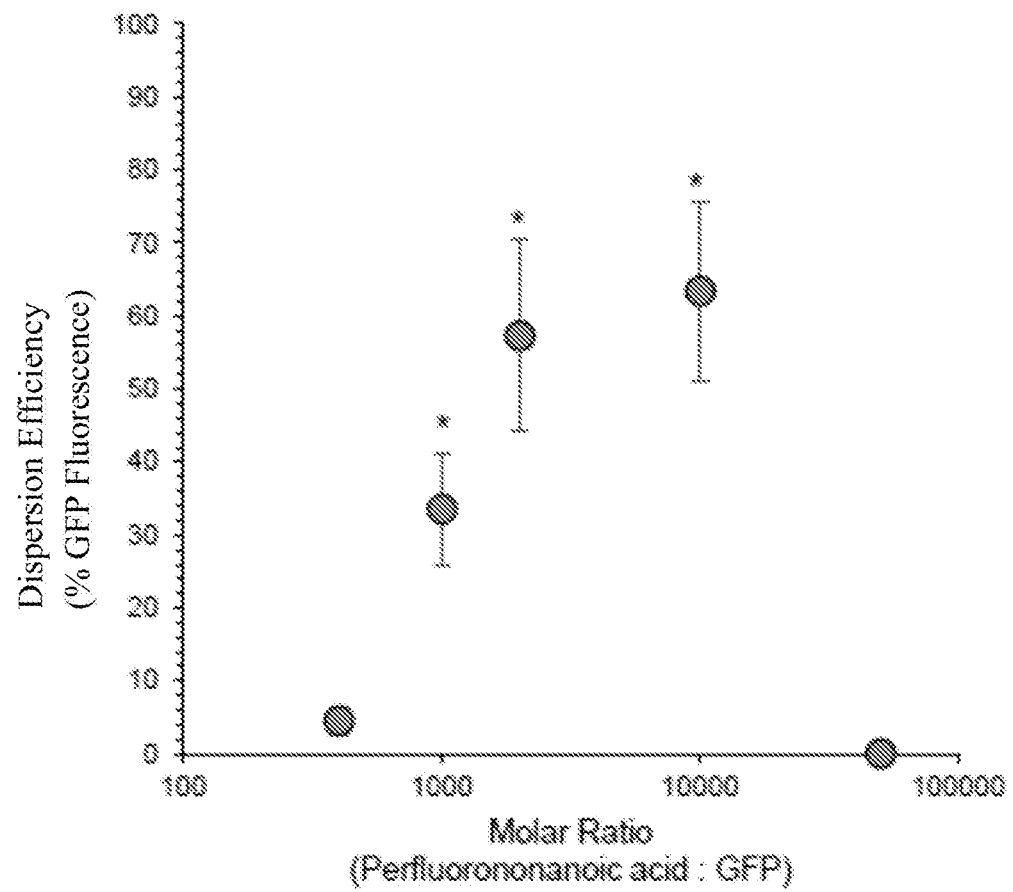
FIG. 16 is a graph that shows the results of optimization of the fluorine-containing cargo solubilizing agent:GFP ratio for maximal GFP loading in the presence of fluorine-containing cargo solubilizing agent #6 (perfluorononanoic acid)

Results were compared to controls to determine % GFP fluorescence. The data shown in FIG. 16 indicates that molar ratios of 2,000 to 10,000:1 are optimal to maximize GFP loading into PFH solvent, achieving a total loading efficiency of ~63%.

For PFH and PFP solvent comparison, 2 mM PFNA was vortexed and sonicated to dissolve into either PFH or PFP on ice. For each condition, 200 ul of adjuvant/PFH or adjuvant/PFP was aliquoted into an Eppendorf tube containing individually dried GFP stocks (1 uM) for 3 replicates. Each tube was parafilmed, vortexed, placed on VWR tube rotator overnight at 4° C., and then centrifuged for 5 min at 4000 rpm. Next, 100 ul of each sample was aliquoted onto a black bottom 96-well plate for fluorescence scan from 500 to 560. The 96-well plate was then placed in 37° C. overnight to dry the PFH and PFP. The dry samples were resuspended in 100 ul PBS and scanned for fluorescence using BioTek Cytation 3 imaging reader.

Figure 17:
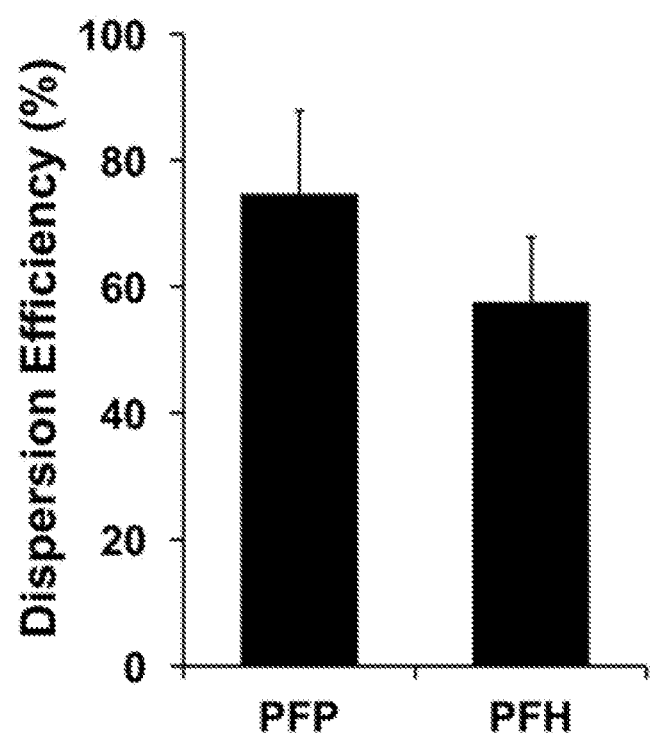
FIG. 17 is a graph showing no significant difference in protein dispersion efficiency with perfluoropentane (PFP) compared to perfluorohexane (PFH) at 2000:1 molar ratio.

The evaluation of protein dispersion with PFNA in PFP shows that there is no significant difference in protein dispersion with PFP compared to PFH at 2000:1 molar ratio (FIG. 17). This confirms that PFH can be used as a model fluorous solvent for subsequent protein-PFNA interaction studies.

Optimization of Ultrasound Power

Fluorine-containing cargo solubilizing agent #6 (perfluorononanoic acid) was prepared at a 2,000:1 fluorine-containing cargo solubilizing agent-to-GFP ratio with the protein in PFP to achieve a total concentration of GFP at 0.25 mg/mL. The fluorine-containing cargo solubilizing agent+PFP+GFP mixture was then added to dry peptide to achieve a 0.5 mg/mL concentration of the peptide, and mixture vigorously vortexed to prepare a turbid, milky emulsion. The emulsion was then added (5% volume to volume, vol/vol) dropwise to ice-cold water stirred at 1,500 revolutions per minute (rpm) to assemble the GFP-loaded peptisomes. Particles were purified overnight via dialysis in 2.5 vol % DMSO. To evaluate GFP release the particles were visualized via bright field and epi-fluorescence imaging after sonication at increasing ultrasound energy; 0-0.8 $W/cm^2$, and at 10% or 20% duty cycle. GFP-loaded peptisomes appeared to be larger in diameter compared to previous formulations (1-5 μm, instead of the previous 0.5 μm). The green fluorescence of GFP is observed in the core of the particle. Particle disruption appears to occur at 0.8 $W/cm^2$ intensity of ultrasound, for both 10% and 20% duty cycles.

GFP-loaded peptisomes (2,000:1 ratio) were prepared as described above. The particles were diluted 10 times into serum-free cell culture media, incubated with A549 cells for 4 hours and then washed. The treated cells were then sonicated with ultrasound (0-1.2 $W/cm^2$, and at 10% or 20% duty cycle) for 90 sec. Following washing and Hoechst staining of the cell nuclei, the intracellular delivery of GFP was visualized via bright field and epi-fluorescence microscopy. Particle disruption and delivery of GFP is visualized to occur at >0.8 $W/cm^2$ intensity of ultrasound at a 10% duty cycle, and at >0.4 $W/cm^2$ for a 20% duty cycle.

Protein-PFNA Complex Interaction Characterization.

For ATR-FTIR, the protein-PFNA interaction was analyzed before and after PFH evaporation. For liquid sample preparation, 1000:1 molar ratio of 50 mM of PFNA in PFH was prepared with 50 uM GFP dry stock. To prevent evaporation, a 1 cm rubber ring was placed around the crystal where the sample was then aliquoted and quickly covered by glass and manual pressure. For dry sample preparation, 2000:1 molar ratio of 100 mM of PFNA in PFH was prepared with 50 uM GFP dry stock (reference dry GFP method). The resulting supernatant post-centrifugation of the sample was aliquoted into a separate Eppendorf tube and placed in 37° C. to dry before analysis. Bruker Vertex V70 instrument and OPUS software was used for measurement and analysis.

For $^{19}F$-NMR, the protein-PFNA interaction was analyzed at 2000:1 and 1000:1 molar ratios. 100 mM or 50 mM of PFNA in PFH was prepared with 50 uM GFP dry stock. The samples were aliquoted into Wilmad-LabGlass Thin Wall Precision NMR sample tubes with Norell coaxial inserts containing the lock signal of $D_2O$. Sample measurements were taken with Bruker AVIII-HD-500 and analyzed with Mnova software.

For circular dichroism (CD), the protein-PFNA interaction was analyzed at 2000:1 molar ratio of 20 mM PFNA in PFH with 10 uM GFP dry stock (reference dry GFP method). The resulting supernatant post-centrifugation of the sample was aliquoted into a separate Eppendorf tube, placed in 37° C. to dry, and then resuspended in CD buffer (50 mM BTP, 150 mM NaF at pH 7.4). GFP control was suspended in CD buffer. The sample measurements were taken by Jasco J-1500 Circular Dichroism Spectrometer.

Figure 18A:
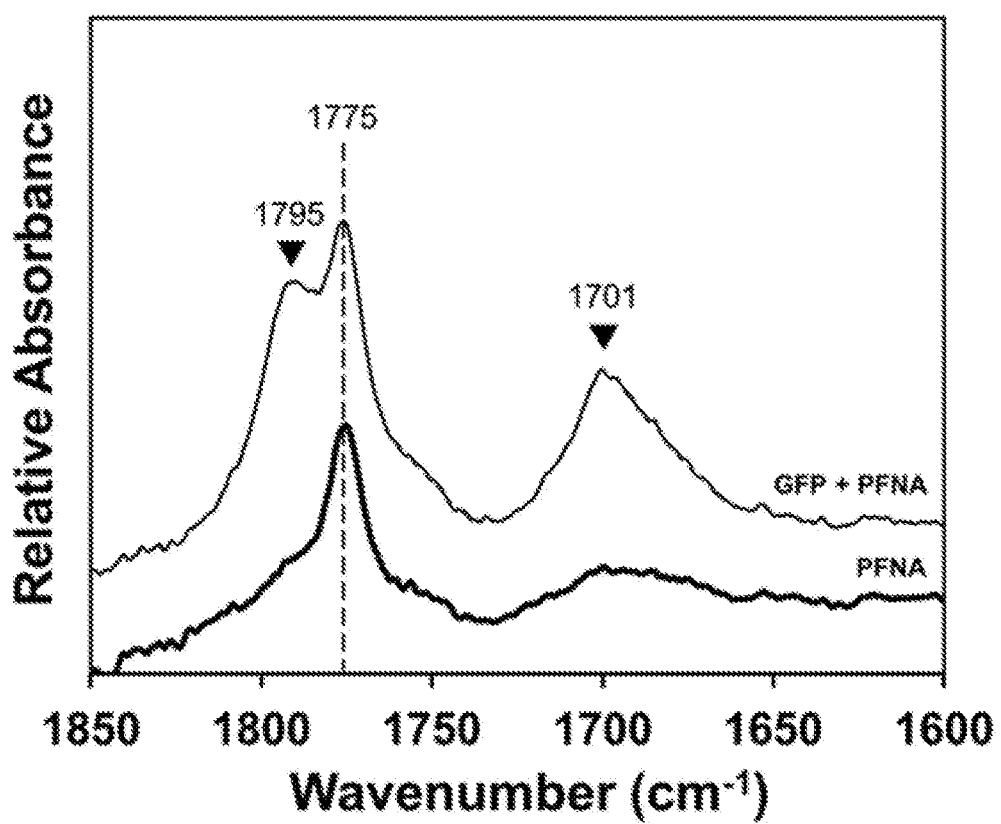
FIG. 18A is a graph showing results of ATR-FTIR analysis of perfluorononanoic (PFNA) and protein-PFNA complex in the fluorous environment.

The protein delivery mechanism of the nanopeptisomes described herein exposes the protein-PFNA complex to three different environments: the fluorous liquid state for encapsulation, the gaseous state during bubble growth, and the aqueous liquid state when delivered into the cell cytoplasm. Using ATR-FTIR, the resulting spectra represents PFNA and protein-PFNA complex in the fluorous environment (FIG. 18A). PFNA has two peaks at 1701 $cm^{-1}$ and 1776 $cm^{-1}$ at wavenumbers indicative of carboxylate stretching regions, similar to perfluorooctanoic acid. With the protein-PFNA interaction, there is an additional peak at 1791 $cm^{-1}$ in the carboxylate stretching region. This 15 $cm^{-1}$ red shift suggests an O—H bond lengthening suggesting that the carboxylic acid on PFNA is interacting with the protein through hydrogen bonds at a molar ratio favorable for protein dispersion. The amide I and II peaks of GFP cannot be seen in the protein-PFNA complex due to the low concentration of protein compared to PFNA present.

Figure 18B:
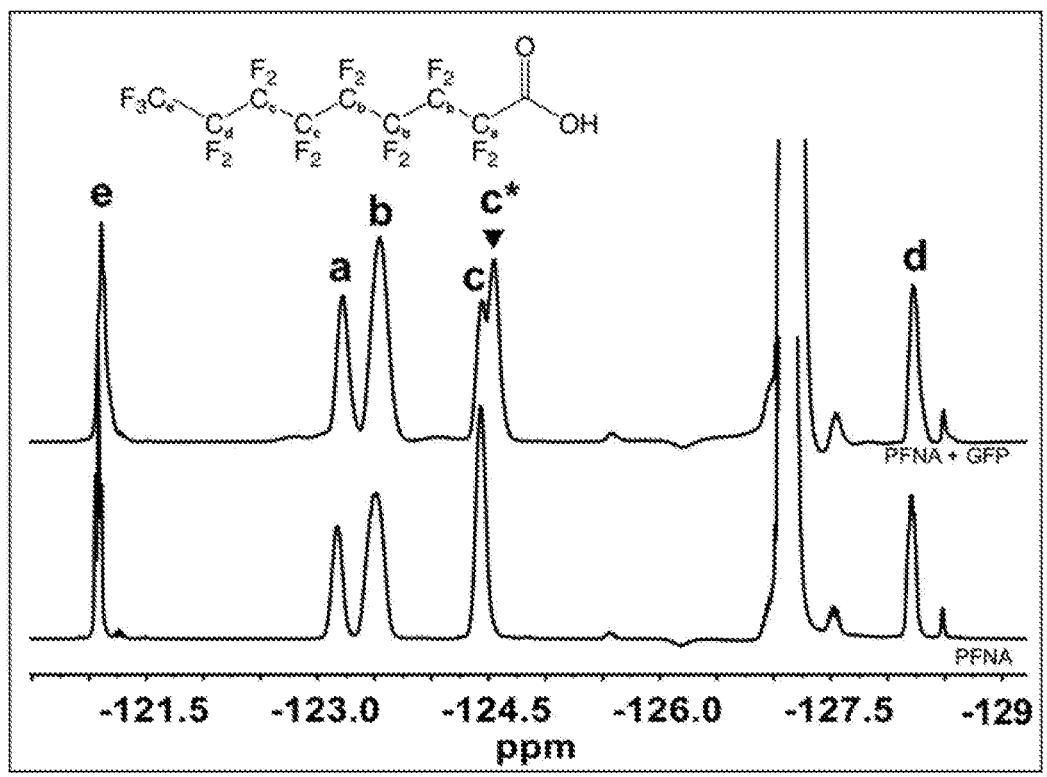
FIG. 18B is a graph showing a $^{19}$F-NMR spectrum of PFNA alone and the protein-PFNA complex in a fluorous environment.

The protein-PFNA favorable interaction is driven by hydrogen bonds. The number of hydrogen bonds necessitating efficient protein dispersion was assessed by $^{19}$F-NMR. The $^{19}$F-NMR spectrum represents PFNA alone and the protein-PFNA complex in a fluorous environment (FIG. 18B). In the presence of protein-PFNA complex, all the chemical shifts remain the same as PFNA alone but with an additional chemical shift at −124.55 ppm. The appearance of a new peak indicates that the CF groups on the PFNA are experiencing an altered environment with the addition of protein. The chemical shift c* at −124.55 ppm is the PFNA hydrogen bonding to the protein, while the chemical shift c at −124.44 ppm is free PFNA. The chemical shift c* is also shown in 1000:1 molar ratio. From this, the number of PFNA molecules per protein was calculated for the initial 2000:1 and 1000:1 molar ratio as 1298:1 and 434:1, respectively, using Lorentzian-Gaussian peak fitting.

Figure 18C:
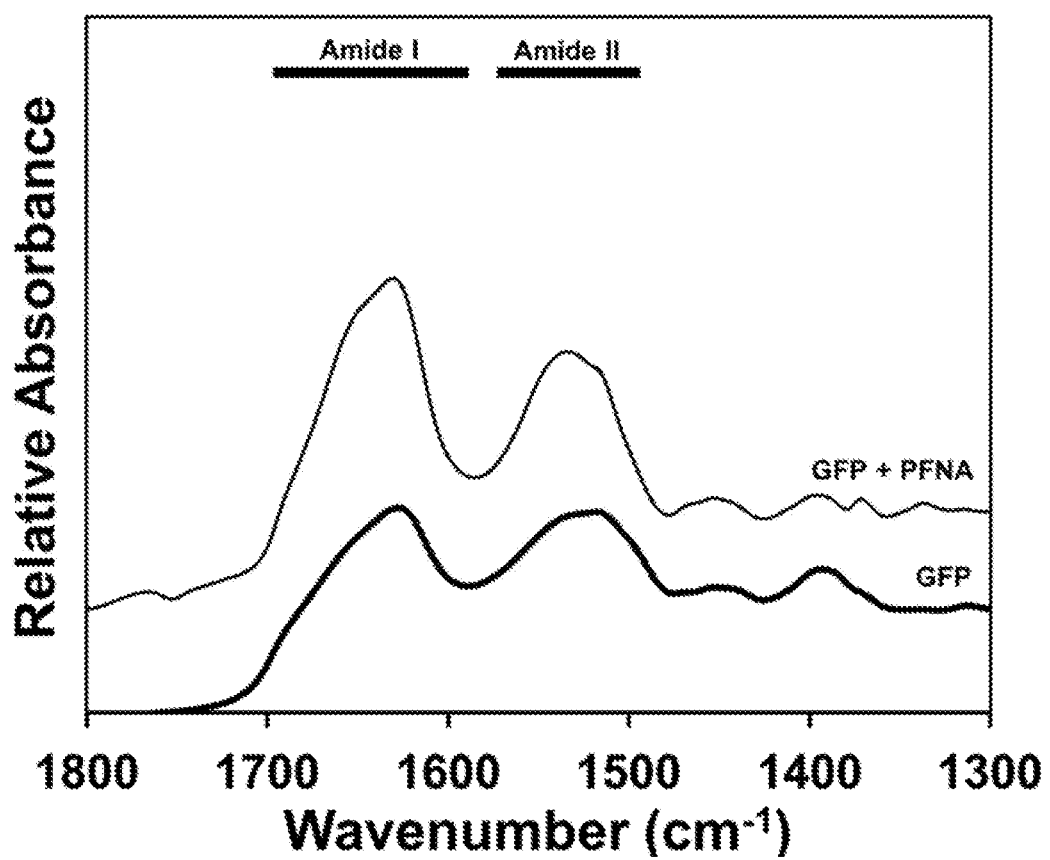
FIG. 18C is a graph showing ATR-FTIR spectra of the interaction of the PFNA on the protein out of the fluorous environment in its dry state.
Figure 18D:
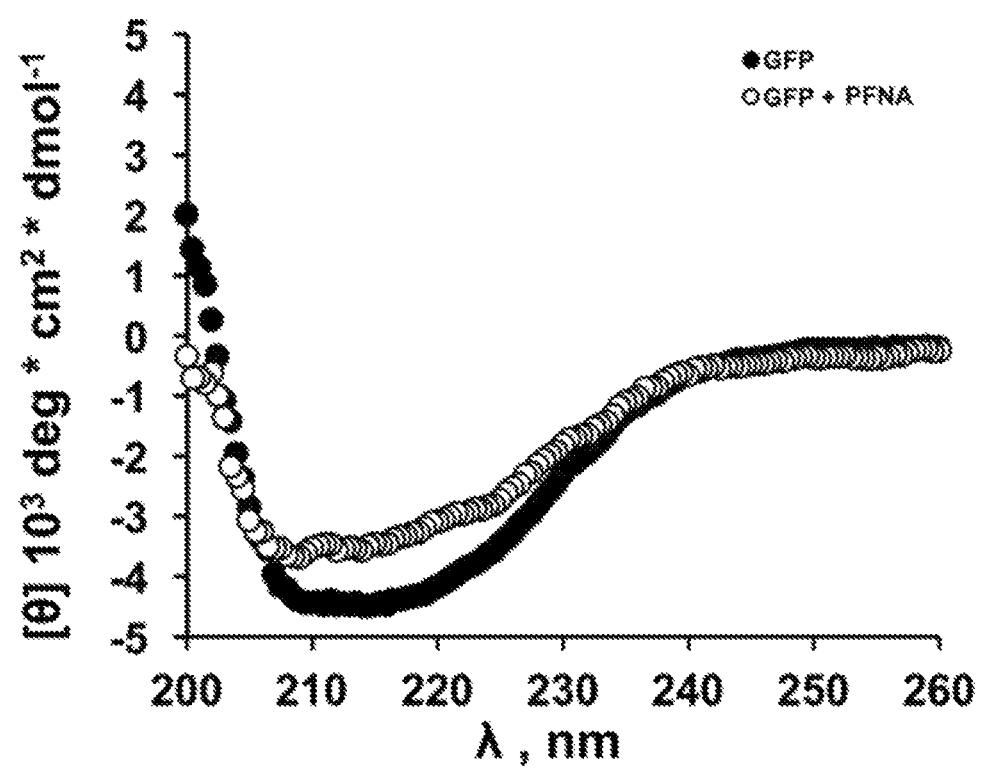
FIG. 18D is a graph showing a circular dichroism (CD) spectrum of the protein-PFNA interaction freed from the fluorous environment into an aqueous environment.

The protein will experience the same fluorous environment and PFNA interaction while encapsulated in the nanopeptisome ($NP_{gfp}$) core. As the $NP_{gfp}$ is activated by ultrasound for protein delivery, the perfluorocarbon core will undergo acoustic droplet vaporization permitting the protein-PFNA transfer from the fluorous environment into a gaseous state during bubble growth subsequently into an aqueous environment post intracellular injection. The ATR-FTIR spectra represents the interaction of the PFNA on the protein out of the fluorous environment in its dry state (FIG. 18C). GFP has amide I and amide II peaks at 1630 $cm^{-1}$ and 1536 $cm^{-1}$, respectively, comparable to previously reported amide I and II peaks. Similarly, the dry protein-PFNA complex shows the same amide I and amide II peaks. No peak shift in the carboxylate stretching region at 1630 $cm^{-1}$ indicates that the hydrogen bonding between protein and PFNA dissociated upon evaporation of the fluorous solvent. The circular dichroism (CD) spectrum represents the protein-PFNA interaction freed from the fluorous environment into an aqueous environment (FIG. 18D). The GFP spectrum is characteristic of the high beta sheet secondary structure from its beta-barrel tertiary structure. When the protein-PFNA complex is transferred into an aqueous buffer, the GFP spectrum resembles that of a folded GFP. This provides evidence that the association and dissociation in and out of the fluorous environment does not alter the structural integrity of the protein. Together, the fluorine-containing cargo solubilizing agent masks the hydrophilic character of protein by means of hydrogen bonds for dispersion within fluorous solvents and readily unmasks the protein upon release from the fluorous solvent without compromising protein structure and function.

Protein Delivery into Cells Via Ultrasound Activation of $NP_{gfp}$ $NP_{gfp}$ were formulated to encapsulate the protein-PFNA complexes within the PFP core using the 2000:1 molar ratio in this example and these were characterized using dynamic light scattering.

To synthesize nanopeptisomes with GFP encapsulated in the PFP core in this example, the core solution of GFP (10 μM), perfluorononanoic acid, and PFP was prepared at 2000:1 molar ratio using the dry GFP method. The amphiphilic peptide, $F_FF_FF_F$GGGCCGGKGRGD-$NH_2$ (SEQ ID NO:49), containing the RGD targeting motif was warmed to room temperature, 1.14 mg was then weighed out and placed in an Eppendorf tube followed by resuspension in 200 μl of GFP/perfluorononanoic acid/PFP by vortexing. Next, deionized (DI) water (3 ml) was aliquoted into a 10 ml round bottom flask submerged in an ice bath on a stir plate spinning at 1200 rpm. A single injection of 150 μl of the amphiphilic peptide+GFP/adjuvant/PFP mixture was aliquoted into the flask ensuring that the pipette tip is submerged in the water without disturbing the stir bar. The emulsion was stirred for 1 hr at 1200 rpm and then transferred into a Slide-A-Lyzer™ dialysis cassette (MWCO 3500 Da) where it was dialyzed overnight with 2.5% DMSO. The resulting $NP_{gfp}$, were dialyzed with water for 1 hr and then collected.

Figure 19:
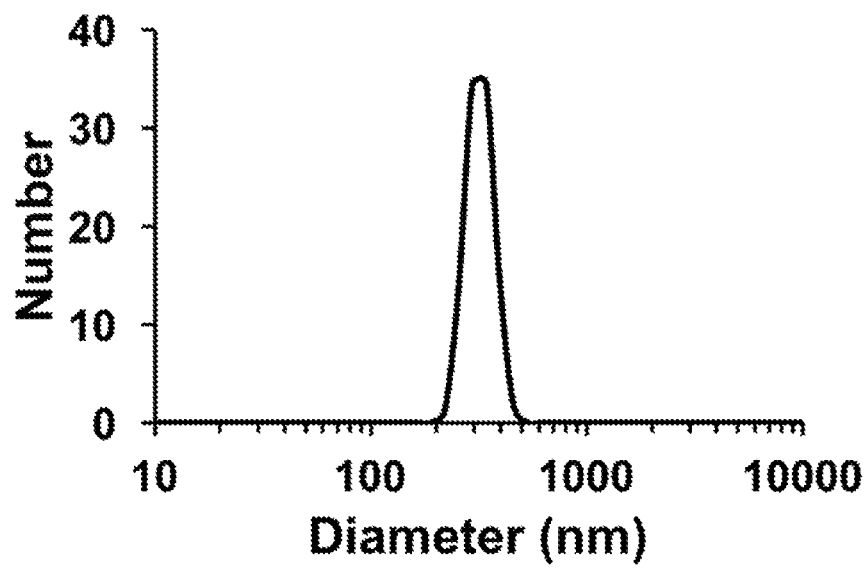
FIG. 19 is a graph showing characterization of the average diameter of GFP-loaded nanopeptisomes (NPgfp) using dynamic light scattering.

The resulting $NP_{gfp}$ were measured via dynamic light scattering (DLS) using a Malvern Zetasizer Nano ZS. For this, $NP_{gfp}$ were diluted 1:10 in TBS buffer (25 mM Tris, 150 mM NaCl at pH 7.4) for analysis. The results demonstrated an average diameter of these $NP_{gfp}$ was 326 nm (FIG. 19).

Confocal microscopy using a Zeiss confocal microscope was performed on $NP_{gfp}$ diluted 1:10 in PBS. Confocal microscopy demonstrated encapsulation of the GFP in the interior of nanopeptisomes and not absorption at the particle surface.

Figure 20A:
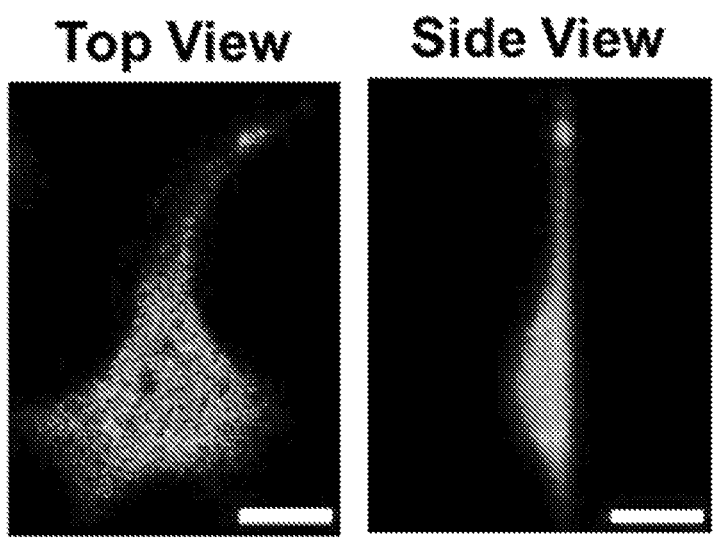
FIG. 20A shows top and side view images of a cell exposed to NPgfp wherein the cells and NPgfp are treated with ultrasound (US) activation to deliver diffuse GFP throughout the cell cytoplasm.

Intracellular Protein Delivery Via $NP_{gfp}$ Aft Ultrasound Vitro was Demonstrated In this example, A549 lung carcinoma cells were contacted with either $NP_{gfp}$ or equivalent concentration of free GFP. Using confocal microscopy, intracellular fluorescence was imaged after ultrasound treatment. Proteins cannot readily diffuse into the intracellular space, even with application of ultrasound, indicated by no GFP fluorescence in +GFP and +US samples. By contrast, contacting A549 lung carcinoma cells with $NP_{gfp}$ followed by treatment with ultrasound results in diffuse GFP throughout the cell cytoplasm (FIG. 20A).

Flow Cytometry

Delivery of GFP intracellularly was quantified via flow cytometry.

For flow cytometry studies, A549 cells were seeded with 1:4 $NP_{gfp}$ in serum free RPMI-1640 media into 12-well plates at $2.5 \times 10^5$ cells/well with a total volume of 1 ml. As a control, A549 cells were seeded with free GFP at a concentration similar to GFP loaded into the nanopeptisomes (2.25 μg/ml) in serum free media into 12-well plates at $2.5 \times 10^5$ cells/well with a total volume of 1 ml. All plates were incubated in the dark shaking at 40 rpm and 37° C. for 4 hours to prevent cell adhesion and allow for integrin-binding of the NP$_{gfp}$. Next, additional 1 ml of serum free media was added to each well before insonation for a total volume of 2 ml/well. Insonation of the samples was performed using Nepagene Sonitron GTS with a plane wave transducer of 1 MHz and 20 mm diameter. The transducer was held with a ring stand and lowered to ~0.25 cm from the bottom of the plate. The ultrasound was applied for 90 seconds with a duty cycle of 20% (2 msec on, 8 msec off) with intensity 0.1, 0.2, 0.5, 1.0, and 2.0 W/cm$^2$. After insonation, the plates were incubated in the dark shaking at 40 rpm and 37° C. for 30 minutes. The cells were transferred from each well into an Eppendorf tube and then centrifuged for 5 min at 2000 rpm. The supernatant was aspirated and then 500 ul of PBS was added. The cells were placed on ice and vortexed before analysis using BD LSR Fortessa flow cytometer (488 nm excitation laser). FlowJo software was used for analysis. Gating was based off of untreated A549 cells to evaluate an increase in GFP fluorescence post-treatment. Each NP$_{gfp}$ treated sample had 5 replicates. Each free GFP treated sample had 3 replicates.

For confocal microscopy, A549 cells were seeded at 5.4×10$^3$ cells/well in a 12-well plate containing a sterilized coverslip in each well and adhered overnight in 37° C. Cells were treated with either 1:5 NP$_{gfp}$ or free GFP (2.25 µg/ml) in serum free media. Next, an additional 1 ml of serum free media was added to each well before insonation for a total volume of 2 ml/well. The ultrasound was applied for 90 seconds with a duty cycle of 20% (2 msec on, 8 msec off) with intensity 2.0 W/cm$^2$. After insonation, the plate was incubated for 15 min at 37° C. and then gently washed with 1 ml serum free media. Cells were fixed with 1 ml of 4% paraformaldehyde in PBS for 10 min at room temperature. Fixative was aspirated and then cell nuclei were stained for 15 min at 37° C. with 1 ml of 2 µg/ml Hoescht 3342 in PBS. Cells were washed with PBS before mounting coverslip on glass slide. Cells were imaged using at 40× magnification using 359 nm and 489 nm single photon lasers for DAPI and GFP, respectively.

Figure 20B:
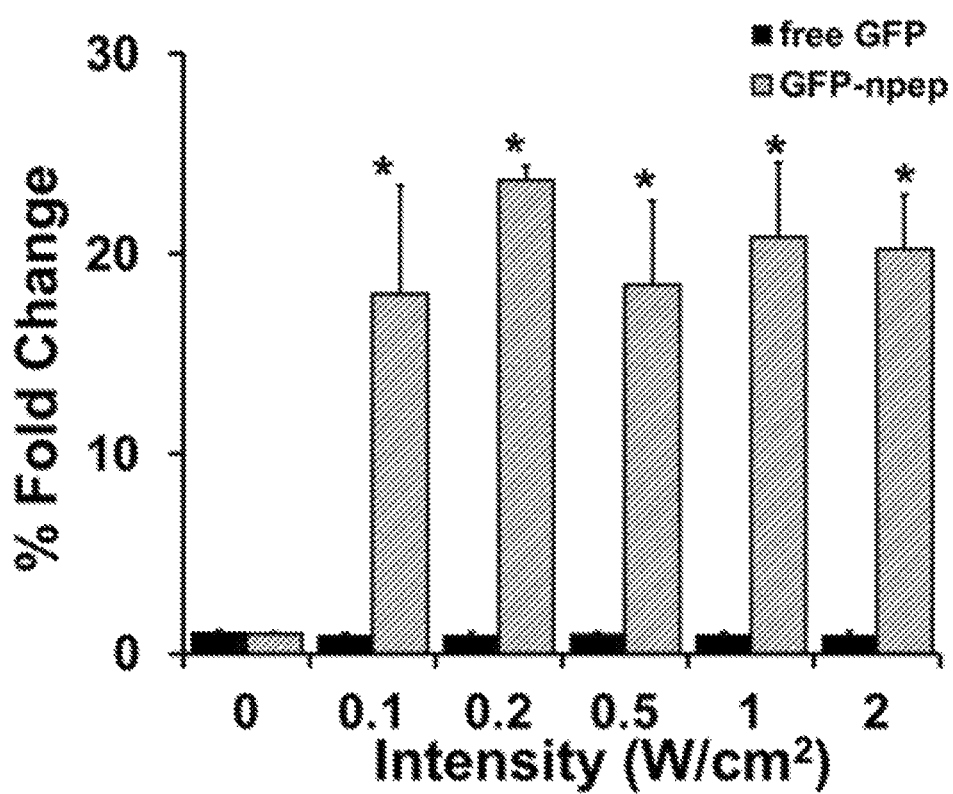
FIG. 20B is a graph showing nanopeptisome (npep)-mediated delivery of GFP into cytoplasm of cells was quantified via flow cytometry with significant GFP delivery via GFP-loaded nanopeptisomes post-US activation at all US intensities applied compared to GFP-loaded nanopeptisomes without ultrasound and compared to free GFP (not associated with peptisomes or nanopeptisomes) with and without ultrasound application.

Results showed significant intracellular GFP delivery at all US intensities tested compared to NP$_{gfp}$ without ultrasound and free GFP with and without ultrasound (FIG. 20B).

To assess viability following treatment with nanopeptisomes and ultrasound, A549 cells were seeded at 1×10$^5$ cells/well on a 12-well plate using RPMI-1640 media supplemented with FBS (10% v/v), L-Gln (2 mM), and gentamycin (0.05 mg/ml). Cells were treated with 1:4 NP$_{gfp}$, in serum-free media for 2 replicates and incubated for 4 hrs at 37° C. before insonation. The cells were treated with ultrasound intensities: 0.1, 0.2, 0.5, 1.0, and 2.0 W/cm$^2$ for 90 seconds at 20% duty cycle in 2 ml media/well and incubated at 37° C. for 30 minutes. Negative control cells were treated with media and positive control cells were treated with 20% DMSO. Then, 1 ml of MTT solution (0.5 mg/ml) in media was added to each well after the removal of treatment media. After a 2 hour incubation, the formazan product was solubilized by adding 1 ml DMSO. The absorbance at 540 nm was read to quantify cell viability using BioTek Cytation 3 imaging reader.

To assess GFP fluorescence post-ultrasound treatment, 1 ml of 1 µM GFP in PBS in wells of a 12-well plate were treated with ultrasound intensities: 0.1, 0.2, 0.5, 1.0, and 2.0 W/cm$^2$ for 90 seconds at 20% duty cycle for 3 replicates per intensity. Negative control and blank of 1 µM GFP in PBS and PBS, respectively, were not treated with ultrasound. The fluorescence at 510 nm was read to quantify any loss of GFP chromophore function using BioTek Cytation 3 imaging reader.

Importantly, cells remained viable under these US intensities and fluorine-containing cargo solubilizing agent concentrations and GFP did not lose fluorescence post-US activation. Thus, NP$_{gfp}$ were capable of ultrasound-activated intracellular protein delivery without compromising cellular viability or protein integrity.

Visualizing NP$_{gfp}$ Tracking and Vaporization by Ultrasound Imaging

Ultrasound waves allow for image-guidance and temporal vaporization of NP$_{gfp}$ for protein delivery.

For ultrasound B-mode and Doppler imaging, NP$_{gfp}$ prepared as above were diluted 1:10 in degassed DI water. A 1.5% agarose phantom was degassed before gelation into mold of 50 ml beaker with 1 cm glass tube imprint (~2 cm deep within gel). The agarose phantom was placed on a block of neoprene, an acoustic absorbing material, in a large bucket of degassed water. NP$_{gfp}$ were imaged in B-mode and Doppler using L7-4 (5 MHz, 3 cycles) and L22-14v (18.5 MHz, 12 cycles) transducers. Using the Verasonics Matlab script, the voltage of the transducers was incrementally increased for image-guided particle tracking in B-mode and for particle acoustic droplet vaporization with Doppler mode. Video images were captured and In-phase quadrature (I/Q) Doppler data was saved throughout the entire experiment. The L7-4, 5 MHz transducer, pressures were measured using a hydrophone. The pressure threshold of acoustic droplet vaporization was performed for three replicates for average ultrasound pressure necessary for droplet vaporization.

Real-time monitoring of NP$_{gfp}$ was captured with B-mode imaging from an 18.5 MHz transducer. Three individual NP$_{gfp}$ were tracked with high echogenicity over six seconds at one second time intervals. This demonstrates that NP$_{gfp}$ are capable of use as ultrasound image-guided particles.

Additionally, the temporal vaporization of NP$_{gfp}$ was captured with Doppler mode imaging from a 5 MHz transducer.

Items

Item 1. An amphiphilic peptide represented by Formula (I):

HB-CL-HP (1) wherein HB is a fluorinated hydrophobic block, CL is a cross-linking motif, and HP is a hydrophilic amino acid sequence, wherein said amphiphilic peptide comprises from 5 to 30 total amino acid residues and wherein said amphiphilic peptide is capable of assembling at the surface of a perfluorocarbon liquid to form a nanopeptisome.

Item 2. The amphiphilic peptide according to item 1, wherein the amphiphilic peptide is represented by Formula (II) or Formula (III):

HB-CL-HP (II), HB-CL-HP—NH$_2$(II) wherein HB is a fluorinated hydrophobic amino acid sequence; CL is a cross-linking motif; and HP is a hydrophilic amino acid sequence.

Item 3. The amphiphilic peptide according to item 1 or 2, wherein HB comprises one pentafluoro-phenylalanine residue at a terminal thereof, one pentafluoro-phenylalanine residue at each terminal thereof, two, three, four or five consecutively connected pentafluoro-phenylalanine residues at a terminal thereof or two, three, four or five consecutively connected pentafluoro-phenylalanine residues at each terminal thereof.

Item 4. The amphiphilic peptide according to any one of items 1, 2, or 3, wherein HP comprises lysine, glycine, arginine, aspartic acid, or any combination thereof.

Item 5. The amphiphilic peptide according to any one of items 1 to 4, wherein HP comprises the sequence KGRGD (SEQ ID NO: 35), where K is lysine, G is glycine, R is arginine, and D is aspartic acid.

Item 6. The amphiphilic peptide according to any one of items 1 to 5, wherein CL comprises at least two cysteines.

Item 7. The amphiphilic peptide according to any one of items 1 to 6, wherein CL comprises GGGCCGG (SEQ ID NO: 46), where G is glycine and C is cysteine.

Item 8. The amphiphilic peptide according to any one of items 1 to 7, wherein said hydrophilic amino acid sequence comprises a conserved targeting motif.

Item 9. The amphiphilic peptide according to any one of items 1 to 8, wherein said hydrophilic amino acid sequence comprises a conserved targeting motif selected from the group consisting of: HGK, RGD, KAR, RSR, KAA, RGRR (SEQ ID NO:1), RGRRS (SEQ ID NO:2), YQLDV (SEQ ID NO:3), EYQ, RPM, PSP, VGVA (SEQ ID NO:4), NGR, CRKRLDRNC (SEQ ID NO:43), EFEEFEIDEEEK (SEQ ID NO:44), and DFEEIPEEYLQ (SEQ ID NO:45).

Item 10. The amphiphilic peptide according to any one of items 1 to 9, wherein said hydrophilic amino acid sequence comprises a hydrophilic amino acid sequence selected from, the group consisting of: GHGKHKNK (SEQ ID NO:5), CRGDKGPDC (SEQ ID NO:6), CKGAKAR (SEQ ID NO:7), CRVSRQNKC (SEQ ID NO:8), CGGERGKSC (SEQ ID NO:9), CRSRKG (SEQ ID NO:10), CKAAKN (SEQ ID NO:11), CRGRRST (SEQ ID NO:12), CRGRRT (SEQ ID NO:50), CEYQLDVE (SEQ ID NO:13), TVRTSAD (SEQ ID NO:14), PIEDRPM (SEQ ID NO:15), ALRDRPM (SEQ ID NO:16), PEKFRPM (SEQ ID NO:17), IKVGKLQ (SEQ ID NO:18), SVSVGMKPSPRP (SEQ ID NO:19), VPEQRPM (SEQ ID NO:20), CAKIDPELC (SEQ ID NO:21), CSNIDARAC (SEQ ID NO:22), RLQLKL (SEQ ID NO:23), PMMRQRPM (SEQ ID NO:24), AKATCPA (SEQ ID NO:25), QPPMEYS (SEQ ID NO:26), SISSLTD (SEQ ID NO:27), FRVGVADV (SEQ ID NO:28). CNGRCVSGCAGRC (SEQ ID NO:29), NWGDRIL (SEQ ID NO:30), CVSNPRWKC (SEQ ID NO:31), CDCRGDCFC (SEQ ID NO:32), YSAYPDSVPMMS (SEQ ID NO:33), and PLASRPM (SEQ ID NO:34).

Item 11. The amphiphilic peptide according to any one of items 1 to 10, wherein said hydrophilic amino acid sequence comprises a hydrophilic amino acid sequence selected from the group consisting of: KGRGD (SEQ ID NO:35), RGDS (SEQ ID NO:36), GRGD (SEQ ID NO:37), GRGDS (SEQ ID NO:38), GRGDSP (SEQ ID NO:39), GRGDSPK (SEQ ID NO:40), GRGDNP (SEQ ID NO:41), and GRGDTP (SEQ ID NO:42).

Item 12. The amphiphilic peptide according to any one of items 1 to 10, wherein said amphiphilic peptide comprises an amphiphilic peptide represented by Formula (IV) or Formula (V): $F_FF_FF_F$GGGCCGGKGRGD (IV) (SEQ ID NO:47), $F_FF_FF_F$GGGCCGGKGRGD-NH$_2$ (V) (SEQ ID NO:49), wherein $F_F$ is pentafluoro-phenylalanine, G is glycine, C is cysteine, K is lysine, G is glycine, R is arginine, and D is aspartic acid.

Item 13. The amphiphilic peptide according to any one of items 1 to 12,
wherein HB is a hydrophobic amino acid sequence comprising from 1 to 10 hydrophobic amino acid residues; CL is a cross-linking motif comprising from about 1 to about 10 amino acid residues; and HP is a hydrophilic amino acid sequence comprising from 3 to 15 hydrophilic amino acids; wherein said amphiphilic peptide comprises from 4 to 30 total amino acid residues and wherein said amphiphilic peptide is capable of assembling at the surface of a perfluorocarbon liquid to form a nanopeptisome.

Item 14. The amphiphilic peptide according to any one of items 1 to 13, wherein HB comprises a fluorinated hydrophobic polymer, wherein the amphiphilic peptide has a molecular weight in the range of about 2000-5000 daltons, wherein the amphiphilic peptide includes at least five amino acid residues, and a total number of no more than 30 amino acid residues, wherein at least two of the amino acid residues are consecutively linked to each other in a chain by a peptide bond.

Item 15. A peptisome comprising: a perfluorocarbon liquid core comprising a perfluorocarbon liquid and a cargo dispersed in the perfluorocarbon liquid; and a plurality of amphiphilic peptides according to any one of items 1 to 14 surrounding the perfluorocarbon liquid core, wherein the amphiphilic peptides are oriented such that groups HB of the amphiphilic peptides are interpolated into the perfluorocarbon liquid of the perfluorocarbon liquid core, the amphiphilic peptides are crosslinked to each other through the cross-linking motif CL, and groups HP extend away from the perfluorocarbon liquid core.

Item 16. The peptisome according to item 15, wherein the peptisome has a diameter in the range from about 1 micron to about 5 microns.

Item 17. The peptisome according to item 15, wherein the peptisome is a nanopeptisome having a diameter in the range from about 250 nanometers to about 1000 nanometers.

Item 18. The peptisome according to item 15, wherein the peptisome is a nanopeptisome having a diameter in the range from about 250 nanometers to about 750 nanometers.

Item 19. The peptisome according to any one of items 15 to 18, wherein a degree of cross-linking of the amphiphilic peptides is about 60% or greater as determined by a colorimetric disulfide formation assay.

Item 20. The peptisome according to any one of items 15 to 19, wherein the cargo is a protein, a peptide, a nucleic acid, a contrast agent, or a small molecule therapeutic.

Item 21. The peptisome according to any one of items 15 to 20, wherein the cargo is a therapeutic agent, a diagnostic agent, a small molecule chemotherapeutic agent, an antithrombotic agent, a protein therapeutic agent, a peptide therapeutic agent, a nucleic acid-based agent, or a gene editing agent.

Item 22. The peptisome according to any one of items 15 to 21, further comprising a fluorine-containing cargo solubilizing agent.

Item 23. The peptisome according to any one of items 15 to 22, wherein the fluorine-containing cargo solubilizing agent is selected from the group consisting of: perfluorooctane ($CF_3(CF_2)_6CF_3$), perfluoroteradecane ($CF_3(CF_2)_{12}CF_3$), trifluoroacetic acid ($CF_3COOH$), pentafluoropropionic acid ($CF_3(CF_2)COOH$), perfluoropentanoic acid ($CF_3(CF_2)_3COOH$), perfluorononanoic acid ($CF_3(CF_2)_7COOH$), perfluorotetradecanoic acid ($CF_3(CF_2)_{12}COOH$), perfluorooctadecanoic acid ($CF_3(CF_2)_{16}COOH$), perfluorocyclohexanecarboxylic acid (($CF_2)_5CFCOOH$), pentafluorophenol (2,3,4,5,6-pentafluorophenol, $C_6F_5OH$), pentafluorobenzaldehyde (2,3,4,5,6-pentafluorobenzaldehyde, $C_6F_5CHO$), or Fmoc-pentafluorophenylalanine (($CF)_5CCH_2C(NH-Fmoc)COOH$, Fmoc-pentafluoro-L-phenylalanine and/or Fmoc-pentafluoro-D-phenylalanine, and a mixture of any two or more thereof.

Item 24. The peptisome according to any one of items 15 to 23, wherein the perfluorocarbon liquid comprises a perfluoropentane, the fluorine-containing cargo solubilizing agent comprises perfluorononanoic acid, the plurality of amphiphilic peptides comprise amphiphilic peptides of formula IV and/or V, and wherein the amphiphilic peptides are crosslinked to each other through the cross-linking motif CL.

Item 25. A method of delivering a cargo to a target cell, comprising the steps of: providing a composition comprising a peptisome according to any one of items to 24; contacting the peptisome and the target cell; and applying ultrasound radiation to activate the peptisome and release the cargo from the peptisome into the target cell.

Item 26. The method according to item 25, wherein the cargo is an active agent selected from the group consisting of: a therapeutic agent, a diagnostic agent, a small molecule chemotherapeutic agent, an anti-thrombotic agent, a protein therapeutic agent, a peptide therapeutic agent, a nucleic acid-based agent, and a gene editing agent.

Item 27. The method according to item 25 or 26, wherein the composition further comprises a pharmaceutically acceptable excipient selected from the group consisting of a vehicle, an adjuvant, a carrier, and a diluent.

Item 28. The method according to any one of items 25, 26, or 27, wherein the cell is in vitro or ex vivo.

Item 29. The method according to any one of items 25, 26, or 27, wherein the cell is a cell of the patient and the method further comprises administering the composition to a patient.

Item 30. The method according to item 29, wherein the patient has cancer and the method comprises applying ultrasound radiation to a diseased tissue of the patient to release the therapeutically active entity from the peptisome.

Item 31. The method according to item 30, wherein the cancer is lung cancer, pancreatic cancer, hepatic cancer, or colorectal cancer.

Item 32. The method according to item 29, wherein the patient has or is suspected of having an atherosclerotic plaque and/or blood clot and the method comprises applying ultrasound radiation to a diseased tissue of the patient to image the atherosclerotic plaque and/or blood clot and/or release the therapeutically active entity from the peptisome.

Any patents or publications mentioned in this specification are incorporated herein by reference to the same extent as if each individual publication is specifically and individually indicated to be incorporated by reference.

The present inventive concept has been described in terms of exemplary principles and embodiments, but those skilled in the art will recognize that variations may be made and equivalents substituted for what is described without departing from the scope and spirit of the disclosure as defined by the following claims.

The invention claimed is:

1. An amphiphilic peptide represented by Formula (III):

HB-CL-HP-NH2        (III)

wherein HB is a fluorinated hydrophobic block consisting of three to five consecutively connected pentafluorinated hydrophobic amino acid residues;
wherein CL is an amino acid sequence consisting of two to 10 amino acid residues, at least two of which are cross-linking cysteine residues;
wherein HP is a hydrophilic amino acid sequence, and
wherein said amphiphilic peptide consists of 8 to 30 total amino acid residues.

2. The amphiphilic peptide according to claim 1, wherein HB consists of three, four or five consecutively connected pentafluoro-phenylalanine residues, and is located at the N-terminal end of the peptide sequence.

3. The amphiphilic peptide according to claim 1, wherein HP comprises lysine, glycine, arginine, aspartic acid, or any combination thereof.

4. The amphiphilic peptide according to claim 1, wherein HP comprises the sequence KGRGD (SEQ ID NO: 35), where K is lysine, G is glycine, R is arginine, and D is aspartic acid.

5. The amphiphilic peptide according to claim 1, wherein CL comprises GGGCCGG (SEQ ID NO: 46), where G is glycine and C is cysteine.

6. The amphiphilic peptide according to claim 1, wherein said hydrophilic amino acid sequence of HP comprises a targeting motif.

7. The amphiphilic peptide according to claim 1, wherein said hydrophilic amino acid sequence comprises a conserved targeting motif selected from the group consisting of: HGK, RGD, KAR, RSR, KAA, RGRR(SEQ ID NO:1), RGRRS (SEQ ID NO:2), YQLDV (SEQ ID NO:3), EYQ, RPM, PSP, VGVA (SEQ ID NO:4), NGR, CRKRLDRNC (SEQ ID NO:43), EFEEFEIDEEEK (SEQ ID NO:44), and DFEEIPEEYLQ (SEQ ID NO:45).

8. The amphiphilic peptide according to claim 1, wherein said hydrophilic amino acid sequence comprises a hydrophilic amino acid sequence selected from the group consisting of: GHGKHKNK (SEQ ID NO:5), CRGDKGPDC (SEQ ID NO:6), CKGAKAR (SEQ ID NO:7), CRVSRQNKC (SEQ ID NO:8), CGGERGKSC (SEQ ID NO:9), CRSRKG (SEQ ID NO:10), CKAAKN (SEQ ID NO:11), CRGRRST (SEQ ID NO:12), CRGRRT (SEQ ID NO:50), CEYQLDVE (SEQ ID NO:13), TVRTSAD (SEQ ID NO:14), PIEDRPM (SEQ ID NO:15), ALRDRPM (SEQ ID NO:16), PEKFRPM (SEQ ID NO:17), IKVGKLQ (SEQ ID NO:18), SVSVGMKPSPRP (SEQ ID NO:19), VPEQRPM (SEQ ID NO:20), CAKIDPELC (SEQ ID NO:21), CSNIDARAC (SEQ ID NO:22), RLQLKL (SEQ ID NO:23), PMMRQRPM (SEQ ID NO:24), AKATCPA (SEQ ID NO:25), QPPMEYS (SEQ ID NO:26), SISSLTD (SEQ ID NO:27), FRVGVADV (SEQ ID NO:28), CNGRCVSGCAGRC (SEQ ID NO:29), NWGDRIL (SEQ ID NO:30), CVSNPRWKC (SEQ ID NO:31), CDCRGDCFC (SEQ ID NO:32), YSAYPDSVPMMS (SEQ ID NO:33), and PLASRPM (SEQ ID NO:34).

9. The amphiphilic peptide according to claim 1, wherein said hydrophilic amino acid sequence comprises a hydrophilic amino acid sequence selected from the group consisting of: KGRGD (SEQ ID NO:35), RGDS (SEQ ID NO:36), GRGD (SEQ ID NO:37), GRGDS (SEQ ID NO:38), GRGDSP (SEQ ID NO:39), GRGDSPK (SEQ ID NO:40), GRGDNP (SEQ ID NO:41), and GRGDTP (SEQ ID NO:42).

10. The amphiphilic peptide according to claim 1, wherein said amphiphilic peptide comprises an amphiphilic peptide represented by Formula (IV) or Formula (V):

$F_F F_F F_F$-GGGCCGGKGRGD (IV) (SEQ ID NO: 47),
$F_F F_F F_F F_F$-GGGCCGGKGRGD-NH2 (V) (SEQ ID NO:49), wherein $F_F$ is pentafluoro-phenylalanine, G is glycine, C is cysteine, K is lysine, G is glycine, R is arginine, and D is aspartic acid.

11. The amphiphilic peptide according to claim 1, wherein said amino acid sequence of CL consists of two to 10 amino acid residues and said hydrophilic amino acid sequence of HP consists of 3 to 15 hydrophilic amino acids;
wherein said amphiphilic peptide consists of 10 to 30 total amino acid residues.

12. The amphiphilic peptide according to claim 1, wherein the amphiphilic peptide has a molecular weight in the range of about 2000-5000 daltons, wherein the amphiphilic peptide includes at least eight amino acid residues, and a total number of no more than 30 amino acid residues, wherein at least two of the amino acid residues are directly connected consecutively by peptide bonds without any intervening amino acid residues.

* * * * *